(12) United States Patent
Crawford et al.

(10) Patent No.: US 8,183,003 B2
(45) Date of Patent: May 22, 2012

(54) POLYMER END GROUP DETECTION

(75) Inventors: Brett E. Crawford, Poway, CA (US);
Jillian R Brown, Poway, CA (US);
Charles A. Glass, San Diego, CA (US)

(73) Assignee: Zacharon Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 13/142,925

(22) PCT Filed: Dec. 31, 2009

(86) PCT No.: PCT/US2009/069946
§ 371 (c)(1),
(2), (4) Date: Sep. 1, 2011

(87) PCT Pub. No.: WO2010/078515
PCT Pub. Date: Jul. 8, 2010

(65) Prior Publication Data
US 2011/0311988 A1   Dec. 22, 2011

Related U.S. Application Data

(60) Provisional application No. 61/142,289, filed on Jan. 2, 2009, provisional application No. 61/160,001, filed on Mar. 13, 2009, provisional application No. 61/164,373, filed on Mar. 27, 2009, provisional application No. 61/223,444, filed on Jul. 7, 2009, provisional application No. 61/236,471, filed on Aug. 24, 2009.

(51) Int. Cl.
*G01N 31/00* (2006.01)
*G01N 33/53* (2006.01)

(52) U.S. Cl. ........ 435/7.21; 435/7.1; 436/501; 436/518; 424/9.1; 424/520; 422/50; 530/300; 530/350

(58) Field of Classification Search ........................ None
See application file for complete search history.

(56) References Cited

U.S. PATENT DOCUMENTS

| | | |
|---|---|---|
| 5,185,245 A | 2/1993 | Heimer |
| 6,117,647 A | 9/2000 | Romisch et al. |
| 2003/0228259 A1 | 12/2003 | Hellerstein |
| 2005/0238536 A1 | 10/2005 | Striepeke et al. |

FOREIGN PATENT DOCUMENTS

| | | |
|---|---|---|
| WO | WO 2007/010089 A2 | 1/2007 |
| WO | WO 2007/010089 A3 | 5/2007 |

OTHER PUBLICATIONS

International search report and written opinion dated Sep. 9, 2010 for PCT/US2009/069946.

*Primary Examiner* — Lisa Cook
(74) *Attorney, Agent, or Firm* — Wilson, Sonsini, Goodrich & Rosati

(57) ABSTRACT

Provided herein are processes of detecting and quantifying the number of polymer end groups in a sample. In particular instances provided herein are processes of detecting.

11 Claims, 18 Drawing Sheets

POLYMER END GROUP DETECTION

CROSS-REFERENCE

This application is filed pursuant to 35 U.S.C. §371 as a United States National Phase Application of International Application Ser. No. PCT/US09/069946, filed 31 Dec. 2009, which claims the benefit of U.S. Provisional Application No. 61/142,289, filed 2 Jan. 2009, U.S. Provisional Application No. 61/160,001, filed 13 Mar. 2009, U.S. Provisional Application No. 61/164,373, filed 27 Mar. 2009, U.S. Provisional Application No. 61/223,444, filed 7 Jul. 2009, and U.S. Provisional Application No. 61/236,471, filed 24 Aug. 2009, all of which are incorporated herein by reference in their entirety.

BACKGROUND OF THE INVENTION

Glycosaminoglycans comprise a reducing end and a non-reducing end. Normal biological processes degrade glycosaminoglycans (such as heparan sulfate which has a normal component of about 50-80 kDa) into monosaccharides. Disorders associated with abnormal glycosaminoglycan degradation, biosynthesis, and/or accumulation can result in an accumulation of oligosaccharides.

SUMMARY OF THE INVENTION

Provided herein are biological samples containing glycosaminoglycans that are transformed into test biological samples by tagging the reducing end of the glycosaminoglycan with a detectable label. The resulting test biological samples are characterized using an analytical device to provide information about both the test biological sample and the original (non-transformed) biological sample.

Provided in certain embodiments herein is a process for diagnosing or diagnosing the severity of a disorder associated with abnormal glycosaminoglycan degradation and/or accumulation in an individual, the process comprising the steps of:
- a. characterizing with an analytical device, within a test biological sample from the individual, a population of glycosaminoglycans that have been tagged with a detectable label at the reducing end of the glycosaminoglycan; and
- b. displaying or recording a characterization of the population of tagged glycosaminoglycans.

In some embodiments, a process described herein further comprises: providing, from an individual, a test biological sample that comprises glycosaminoglycans. The sample is optionally provided by a medical practitioner, technician or institution that obtained the sample, or is directly obtained from the individual. In some embodiments, any process described herein comprises tagging the reducing end of a representative portion of the glycosaminoglycans in the population of glycosaminoglycans within the biological sample with the detectable label to provide the population of tagged glycosaminoglycans.

In some embodiments, characterizing the population of tagged glycosaminoglycans according to any process described herein comprises quantifying the tagged glycosaminoglycans.

In certain embodiments, characterizing the population of tagged glycosaminoglycans includes:
- a. detecting a signal from the tagged glycosaminoglycans in the test biological sample;
- b. quantifying the intensity of the signal; and
- c. comparing the quantified signal intensity in the test biological sample with a quantified signal intensity from tagged glycosaminoglycans in a control biological sample that has been treated in a manner substantially similar to the test biological sample.

In some embodiments, an analytical device utilized in any process described herein comprises one or more of a detection device and/or a purification device including, e.g., one or more of a thin layer chromatographic device, a high performance liquid chromatographic (HPLC) device, a mass spectrometric (MS) device, a gel electrophoresis device, a dot blot device, an immune-detection device, an NMR device, a gas chromatographic device, or a combination thereof.

In certain embodiments, displaying or recording the characterization of the population of tagged glycosaminoglycans comprises displaying or recording the comparison of the quantified signal intensity of the tagged glycosaminoglycans in the test biological sample to the amount of tagged glycosaminoglycans present in the control biological sample. In specific embodiments, the control biological sample was provided from an individual that does not have mucopolysaccharidosis. In some embodiments, the control biological sample was provided from an individual that has mucopolysaccharidosis (MPS). In specific embodiments, the control biological sample was provided from an individual that has MPS I, MPS II, MPS IIIA, MPS IIIB, MPS IIIC, MPS IIID, MPS IVA, MPS IVB, MPS VI, MPS VII, MPS IX or a combination thereof.

In some embodiments, characterizing the population of tagged glycosaminoglycans according to any process described herein comprises detecting different types of tagged glycosaminoglycans within the population of tagged glycosaminoglycans. In certain embodiments, characterizing the population of tagged glycosaminoglycans further comprises quantifying the amount of one or more of the different types of tagged glycosaminoglycans. In specific embodiments, one or more different types of tagged glycosaminoglycans are one or more different tagged heparan sulfate fragments. In some embodiments, the one or more different types of tagged glycosaminoglycans are one or more different tagged chondroitin sulfate fragments, one or more different tagged dermatan sulfate fragments, one or more different tagged heparan sulfate fragments, one or more different tagged keratan sulfate fragments, one or more different tagged hyaluronan fragments, or a combination thereof.

In certain embodiments, detection and quantification of tagged glycosaminoglycans (e.g., different types of tagged glycosaminoglycans) is achieved using thin layer chromatography (TLC) techniques, high performance liquid chromatography (HPLC) techniques, mass spectrometry (MS) techniques, electrophoresis techniques, dot blot techniques, immune-detection techniques, or a combination thereof. In some embodiments, characterization of the population of tagged glycosaminoglycans comprises comparing the amount of one or more of the different types of tagged glycosaminoglycans to an amount of one or more of the different types of tagged glycosaminoglycans of a control biological sample that has been treated in a manner substantially similar to the test biological sample. In some embodiments, prior to treatment, the control biological sample was provided from an individual that does not have mucopolysaccharidosis. In certain embodiments, prior to treatment, the control biological sample was provided from an individual that has mucopolysaccharidosis. In specific embodiments, the control biological sample was provided from an individual that has MPS I, MPS II, MPS IIIA, MPS IIIB, MPS IIIC, MPS IIID, MPS IVA, MPS IVB, MPS VI, MPS VII, MPS IX, or a combination thereof.

In some embodiments, any process described herein comprises collecting the glycosaminoglycans from the test biological sample prior to tagging the reducing end of the glycosaminoglycans. In various embodiments, any suitable detectable label is used in any process described herein including, by way of non-limiting example, a mass label, affinity label, radiolabel, chromophore, or a fluorescent label. In specific embodiments, a fluorescent label utilized in a process described herein is 2-aminobenzamide (2-AB), 2-aminoacridone (AMAC), or 8-amino-1,3,6-naphthalene trisulfonic acid (ANTS).

In some embodiments, the population of glycosaminoglycans within a biological sample that are tagged with a detectable label are heparan sulfate and heparan sulfate fragments. In some embodiments, the population of glycosaminoglycans within the biological sample that are tagged with a detectable label are heparan sulfate fragments.

In certain embodiments, a disorder, or the severity thereof, diagnosed according to any process herein associated with abnormal glycosaminoglycan degradation is a lysosomal storage disease. In some embodiments, the disorder associated with abnormal glycosaminoglycan degradation is mucopolysaccharidosis (MPS). In specific embodiments, the mucopolysaccharidosis (MPS) is MPS I, MPS II, MPS IIIA, MPS IIIB, MPS IIIC, MPS IIID, MPS IVA, MPS IVB, MPS VI, MPS VII, MPS IX, or a combination thereof.

In some embodiments, a diagnostic method provided herein comprises using quantified signal intensity in the test biological sample relative to the quantified signal intensity in the control biological sample as a measure of the severity of the disorder associated with abnormal glycosaminoglycan degradation in the individual.

Provided in certain embodiments herein is a process for diagnosing or diagnosing the severity of a disorder associated with abnormal glycosaminoglycan biosynthesis, abnormal glycosaminoglycan degradation and/or glycosaminoglycan accumulation in an individual, the process comprising:
 a. providing a test biological sample from the individual, the biological sample comprising glycosaminoglycans;
 b. detecting and/or quantifying the glycosaminoglycan end groups of a population of glycosaminoglycans within the test biological sample; and
 c. displaying or recording a quantification of the population of glycosaminoglycans.

In some embodiments, the population of glycosaminoglycans comprises heparan sulfate, one or more heparan sulfate fragments, or a combination thereof. In certain embodiments, quantifying the glycosaminoglycan end groups of a population of glycosaminoglycans comprises (i) tagging a representative portion of the glycosaminoglycan end groups of the population of glycosaminoglycans with detectable labels; and (ii) quantifying the detectable labels attached to the glycosaminoglycan end groups of the population of glycosaminoglycans. In some embodiments, quantifying the glycosaminoglycan end groups of a population of glycosaminoglycans comprises (i) contacting the test biological sample with agents that selectively bind a glycosaminoglycan end group of the population of glycosaminoglycans; and (ii) quantifying the amount of glycosaminoglycan end groups bound to the agents. In some embodiments, agents that selectively bind a glycosaminoglycan end group of the population of glycosaminoglycans include, by way of non-limiting example, probes, antibodies, or a combination thereof. In various embodiments, quantification of glycosaminoglycans, or the end groups thereof, according to any process described herein is achieved in a quantitative or qualitative manner.

In some embodiments, the population of glycosaminoglycans whose end groups are quantified and/or detected are or include one or more different chondroitin sulfate fragments, one or more different dermatan sulfate fragments, one or more different heparan sulfate fragments, one or more different keratan sulfate fragments, one or more different hyaluronan fragments, or a combination thereof. In specific embodiments, the population of glycosaminoglycans whose end groups are quantified and/or detected are or include one or more different tagged chondroitin sulfate fragments, one or more different tagged dermatan sulfate fragments, one or more different tagged heparan sulfate fragments, one or more different tagged keratan sulfate fragments, one or more different tagged hyaluronan fragments, or a combination thereof.

Provided in some embodiments here in is a method of treating (or monitoring the treatment of) a disorder associated with abnormal glycosaminoglycan degradation or accumulation in an individual, the method comprising:
 a. administering an agent that modulates glycosaminoglycan biosynthesis or a glycosaminoglycan accumulation inhibitor to an individual in need thereof;
 b. characterizing, within a test biological sample from the individual, a population of glycosaminoglycans that have been tagged with a detectable label at the reducing end of the glycosaminoglycan; and
 c. displaying or recording a characterization of the population of tagged glycosaminoglycans.

In certain embodiments, the agent that modulates glycosaminoglycan biosynthesis is an agent that selectively modulates heparan sulfate biosynthesis, an agent that selectively modulates chondroitin sulfate biosynthesis, an agent that selectively modulates dermatan sulfate biosynthesis, an agent that selectively modulates keratan sulfate biosynthesis, an agent that selectively modulates hyaluronan biosynthesis, or a combination thereof. In some embodiments, an agent that modulates glycosaminoglycan biosynthesis promotes or activates glycosaminoglycan synthesis (e.g., proteoglycan linker synthesis, saccharide polymerization, sulfation, phosphorylation, or the like) or degradation.

In some embodiments, a method provided herein is used for treating a disorder associated with glycosaminoglycan degradation that is a lysosomal storage disease. In specific embodiments, the lysosomal storage disease is mucopolysaccharidosis (MPS). In more specific embodiments, the mucopolysaccharidosis (MPS) is MPS I, MPS II, MPS IIIA, MPS IIIB, MPS IIIC, MPS IIID, MPS IVA, MPS IVB, MPS VI, MPS VII, MPS IX, or a combination thereof. In certain embodiments, the disorder associated with glycosaminoglycan degradation is cancer.

Provided in certain embodiments herein is a process for identifying an agent that inhibits the accumulation of glycosaminoglycans in a cell (including, e.g., in a cell in an individual), the process comprising:
 a. contacting a plurality of mammalian cells with a compound (e.g., candidate or test compound), the plurality of mammalian cells being of a cell line that accumulates an abnormal amount of glycosaminoglycans;
 b. incubating the mammalian cells with the compound;
 c. characterizing, within a sample from the plurality of mammalian cells, a population of glycosaminoglycans that have been tagged with a detectable label at the reducing end of each glycosaminoglycan; and
 d. displaying or recording a characterization of the population of tagged glycosaminoglycans.

In some embodiments, the cell line that accumulates an abnormal amount of glycosaminoglycans being a human mucopolysaccharidosis (MPS) cell line. In specific embodiments, the mucopolysaccharidosis (MPS) is MPS I, MPS II, MPS IIIA, MPS IIIB, MPS IIIC, MPS IIID, MPS IVA, MPS IVB, MPS VI, MPS VII, MPS IX, or a combination thereof. In more specific embodiments, the compound is a polynucleotide, a polypeptide, or a compound having a molecular weight of less than 2,000 g/mol. In various embodiments, displaying and recording techniques include any of those described herein. In some embodiments, an agent that inhibits the accumulation of glycosaminoglycans in a cell is identified as an agent that slows the rate of glycosaminoglycans in the cells, an agent that arrests or stops the accumulation of glycosaminoglycans in the cells, or reverses the accumulation of glycosaminoglycans in the cells. In some embodiments, the process further comprises determining a rate of glycosaminoglycan accumulation in the cells prior to contact with the compound. In certain embodiments, the process comprises comparing the rate of glycosaminoglycan accumulation in the cells after contact with the compound to the same cells prior to contact with the compound or substantially identical cells that have not been contacted with the compound and/or an agent that inhibits the accumulation of glycosaminoglycans.

Provided in certain embodiments herein is a process for diagnosing or determining the severity of abnormal glycosaminoglycan accumulation or a disorder associated with abnormal glycosaminoglycan degradation in an individual, the process comprising the steps of:
  a. quantifying with an analytical device, within or from within a test biological sample from the individual, the amount of a population of glycosaminoglycans that have been tagged with a detectable label at the reducing end of the glycosaminoglycan; and
  b. displaying or recording a quantification of the amount of the population of tagged glycosaminoglycans
whereby the quantification of the population of tagged glycosaminoglycans is utilized to diagnose or determine the severity of abnormal glycosaminoglycan accumulation or a disorder associated with abnormal glycosaminoglycan degradation.

In certain embodiments, any process described herein further comprising the step of:
  a. collecting from the individual a biological sample that comprises glycosaminoglycans; and
  b. tagging the reducing end of a representative portion of the glycosaminoglycans in the population of glycosaminoglycans within the biological sample with the detectable label to provide the population of tagged glycosaminoglycans.

In further or alternative embodiments, any process described herein comprises quantifying the amount of tagged glycosaminoglycans by:
  a. detecting a signal from the tagged glycosaminoglycans in the test biological sample;
  b. quantifying the intensity of the signal; and
  c. comparing the quantified signal intensity in the test biological sample with a quantified signal intensity from tagged glycosaminoglycans in a control biological sample that has been treated in a manner substantially similar to the test biological sample.

In some embodiments, the analytical device used in any process described herein comprises one or more of a thin layer chromatographic device, a high performance liquid chromatographic (HPLC) device, a mass spectrometric (MS) device, a gel electrophoresis device, a dot blot device, an immune-detection device, an NMR device, a gas chromatographic device, or a combination thereof.

In certain embodiments, the one or more different types of tagged glycosaminoglycans are one or more different tagged heparan sulfate fragments. In some embodiments, quantifying the amount of a population of glycosaminoglycans that have been tagged comprises separately quantifying the amount of a population of one or more different tagged chondroitin sulfate fragments, one or more different tagged dermatan sulfate fragments, one or more different tagged heparan sulfate fragments, one or more different tagged keratan sulfate fragments, one or more different tagged hyaluronan fragments, or a combination thereof. In some embodiments, populations of glycosaminoglycans within the biological sample that are tagged with a detectable label comprise heparan sulfate and heparan sulfate fragments. In some embodiments, a disorder associated with abnormal glycosaminoglycan degradation is a lysosomal storage disease. In certain embodiments, a disorder associated with abnormal glycosaminoglycan degradation is mucopolysaccharidosis (MPS). In some embodiments, the mucopolysaccharidosis (MPS) is MPS I, MPS II, MPS IIIA, MPS IIIB, MPS IIIC, MPS IIID, MPS IVA, MPS IVB, MPS VI, MPS VII, MPS IX, or a combination thereof.

In certain embodiments, any process described herein further comprises collecting the glycosaminoglycans from the test biological sample prior to tagging the reducing end of the glycosaminoglycans. In certain embodiments, a detectable label utilized herein is a mass label, affinity label, radiolabel, chromophore, or a fluorescent label. In specific embodiments, a fluorescent label utilized in any process herein is 2-aminobenzamide (2-AB), 2-aminoacridone (AMAC), Bodipy, or 8-amino-1,3,6-naphthalene trisulfonic acid (ANTS).

In some embodiments, any process described herein further comprises using the quantified signal intensity in the test biological sample relative to the quantified signal intensity in the control biological sample as a quantification of the severity of the disorder associated with abnormal glycosaminoglycan degradation in the individual.

Provided in certain embodiments herein is a method of monitoring abnormal glycosaminoglycan accumulation, or a disorder associated therewith, in an individual, the method comprising:
  (a) administering an agent that modulates glycosaminoglycan biosynthesis to an individual in need thereof;
  (b) quantifying, within or from within a test biological sample from the individual, a population of glycosaminoglycans that have been tagged with a detectable label at the reducing end of the glycosaminoglycan; and
  (c) displaying or recording a quantification of the population of tagged glycosaminoglycans
whereby the quantification of the population of tagged glycosaminoglycans is utilized to monitor abnormal glycosaminoglycan accumulation, or a disorder associated therewith.

In certain embodiments, the agent that modulates glycosaminoglycan biosynthesis is an agent that selectively modulates heparan sulfate biosynthesis, an agent that selectively modulates chondroitin sulfate biosynthesis, an agent that selectively modulates dermatan sulfate biosynthesis, an agent that selectively modulates keratan sulfate biosynthesis, an agent that selectively modulates hyaluronan biosynthesis, or a combination thereof.

In various embodiments, abnormal accumulation of glycosaminoglycans includes the accumulation of abnormal (e.g., non-wild type) glycans and/or the accumulation of abnormal amounts of glycans (e.g., wild type glycans and/or non-wild type glycans). In some embodiments, the disorder associated with glycosaminoglycan accumulation is a lysosomal storage disease. In certain embodiments, lysosomal storage disease is mucopolysaccharidosis (MPS). In specific embodiments, the mucopolysaccharidosis (MPS) is MPS I, MPS II, MPS IIIA, MPS IIIB, MPS IIIC, MPS IIID, MPS IVA, MPS IVB, MPS VI, MPS VII, MPS IX, or a combination thereof. In some embodiments, the disorder associated with abnormal glycosaminoglycan accumulation is cancer.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4 also illustrates the detection of variation in accumulation severity.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Provided in certain embodiments herein are processes of detecting polymeric compounds (e.g., glycans) in a sample by detecting the end units of the polymeric compounds (e.g., glycans). In specific embodiments, the polymeric compounds detected are glycosaminoglycans (GAGs). In some embodiments, provided herein are processes of quantifying the amount of polymeric compounds (e.g., glycans) in a sample by quantifying the amount of polymeric compound (e.g., glycan) end units in the sample. In specific embodiments, the polymeric compounds (e.g., glycans) quantified are glycosaminoglycans (GAGs). In some embodiments, such processes are utilized in any suitable process, e.g., a process of diagnosing an individual with a disorder associated with abnormal degradation and/or accumulation of a polymeric compound (e.g., glycosaminoglycan), a process of identifying compounds suitable for treating disorders associated with abnormal degradation and/or accumulation of a polymeric compound (e.g., glycosaminoglycan), a process of determining the severity of a disorder associated with abnormal degradation and/or accumulation of a polymeric compound (e.g., glycosaminoglycan), in a method of treating a disorder associated with abnormal degradation and/or accumulation of a polymeric compound (e.g., glycosaminoglycan) (e.g., as a manner of monitoring the progress, response, and/or efficacy of the treatment), or the like. As used herein, an individual includes mammal, such as humans, that produce glycosaminoglycans.

Figure 1:
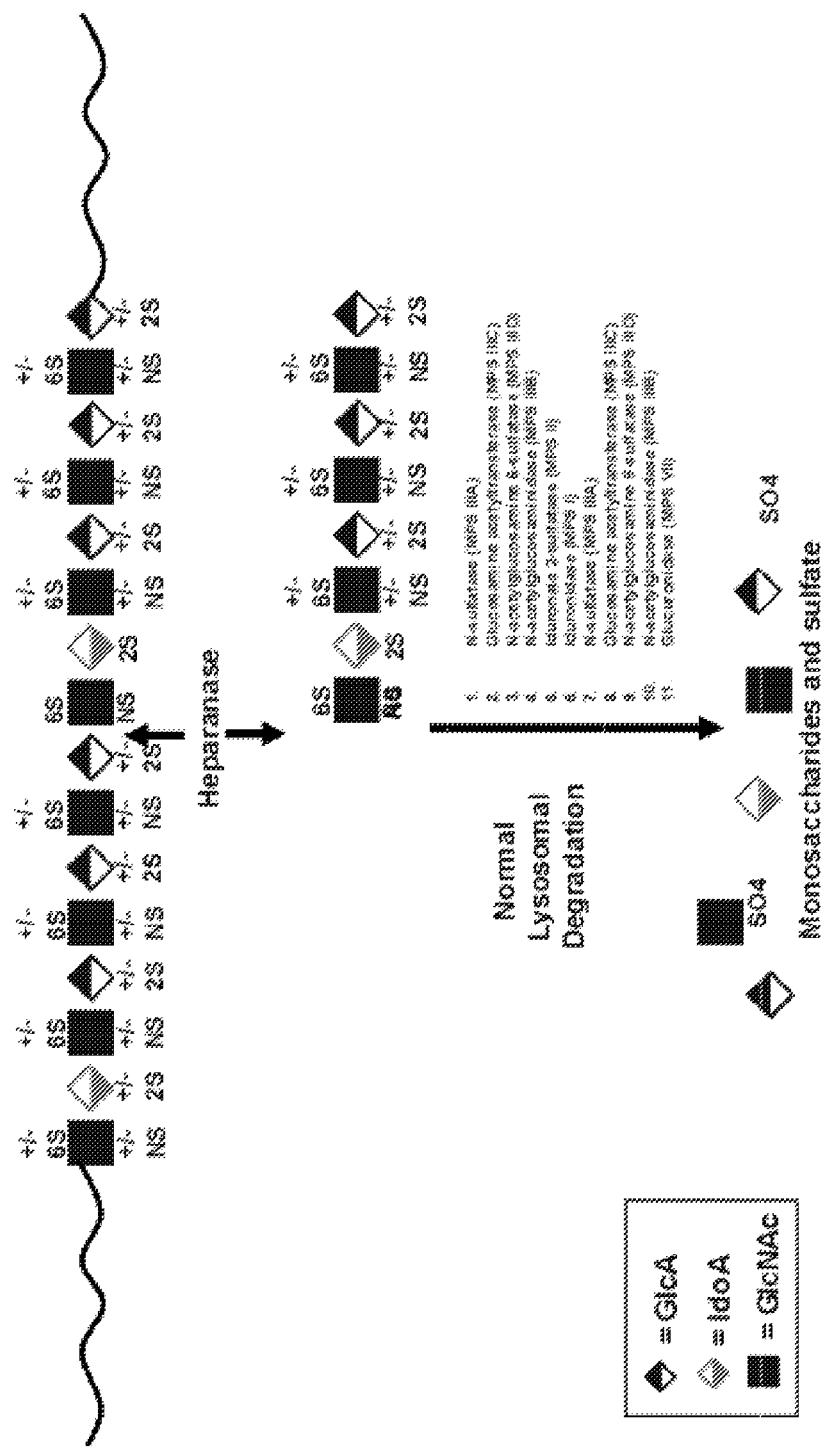
FIG. 1 illustrates normal lysosomal GAG degradation.
Figure 2:
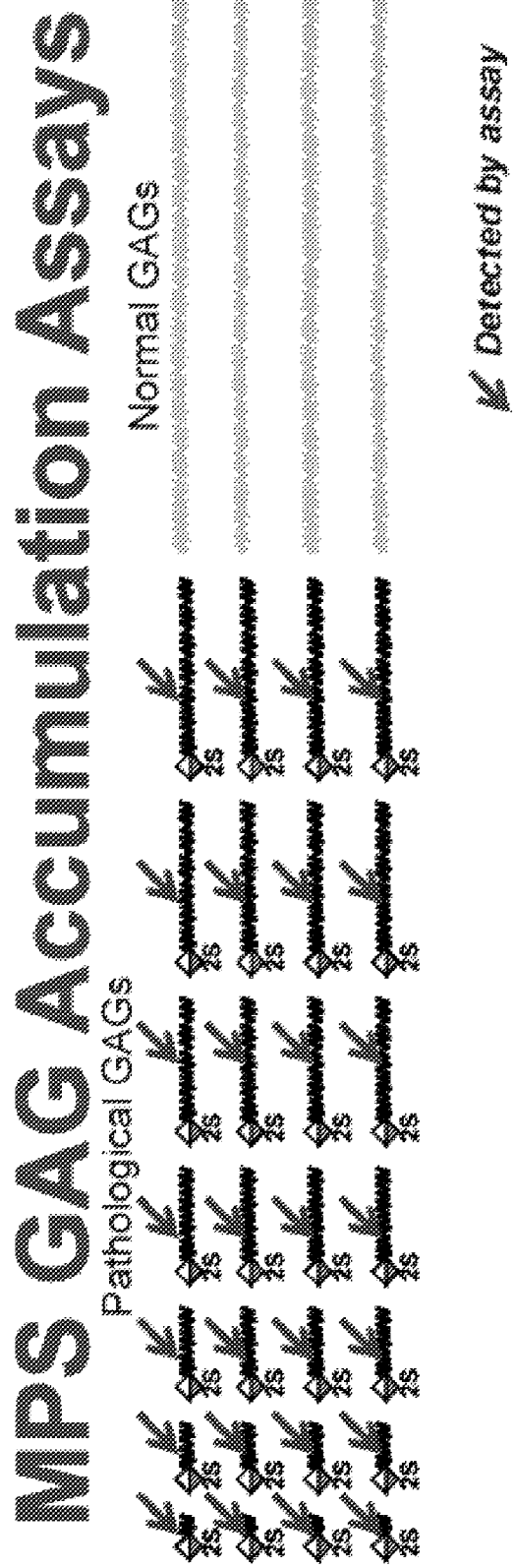
FIG. 2 illustrates GAG accumulation in individuals with MPS.
Figure 3:
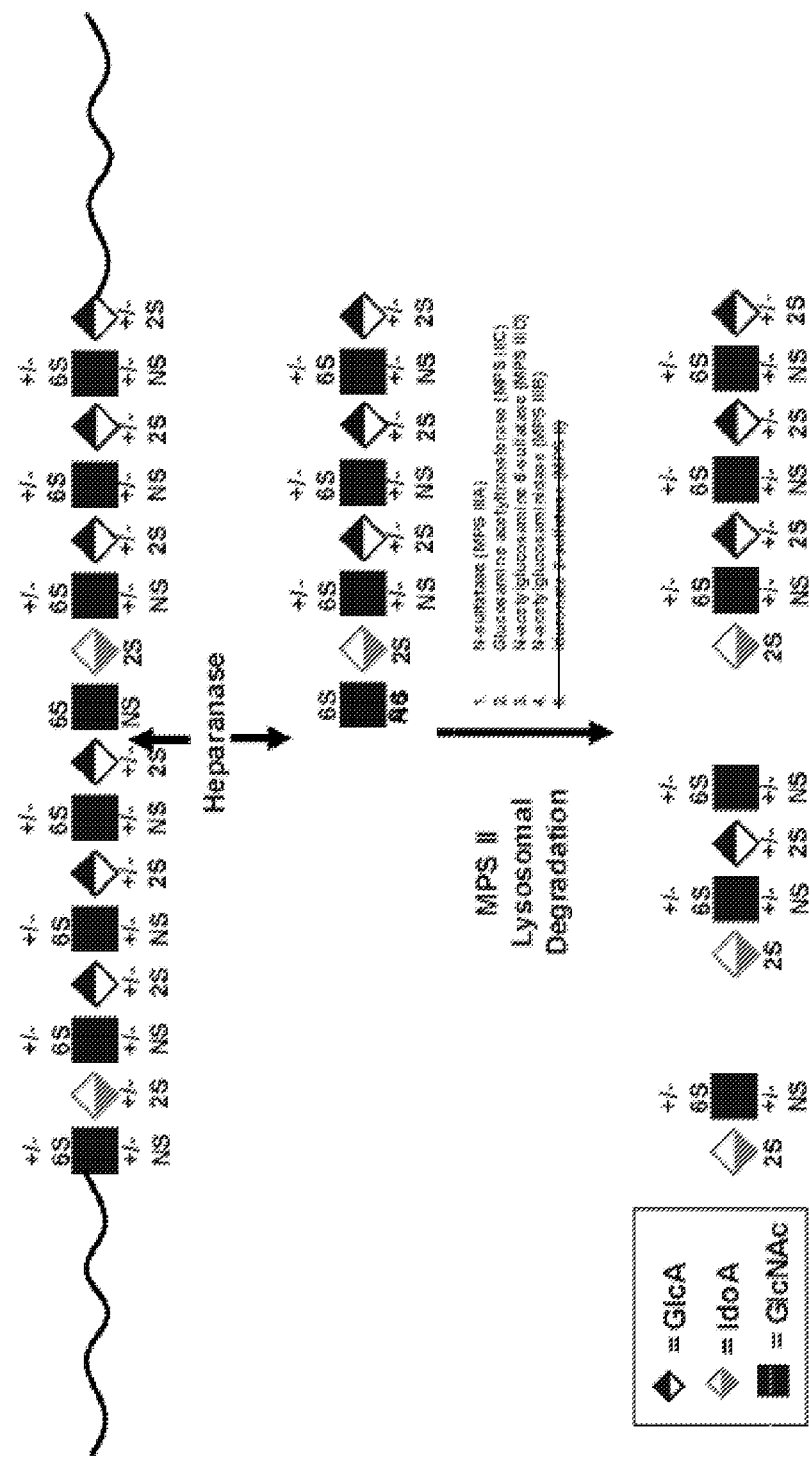
FIG. 3 illustrates lysosomal GAG degradation in individuals with MPS II.
Figure 4:
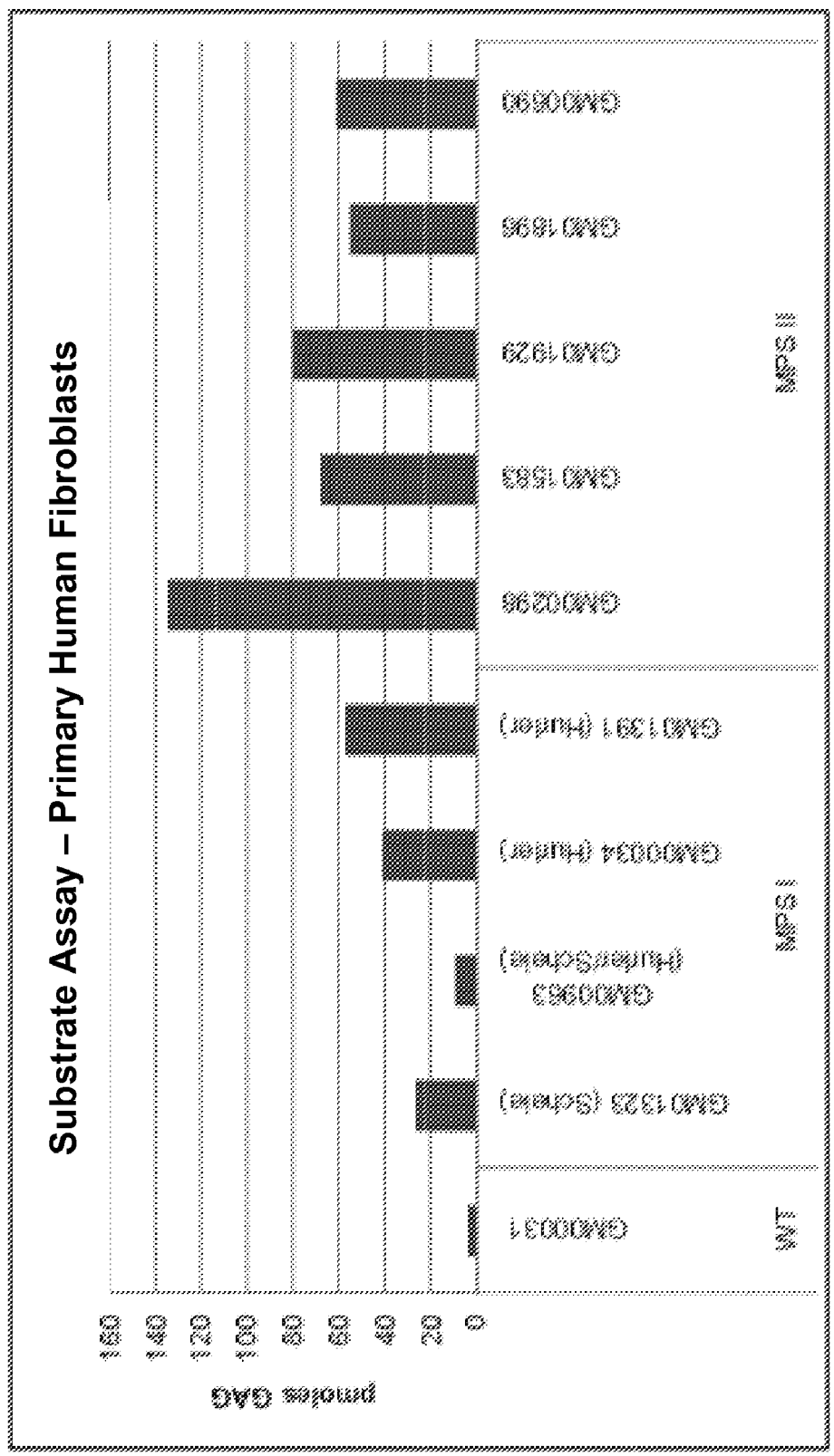
FIG. 4 illustrates GAG accumulation in various human fibroblast lines, including wild type, MPS I, and MPS II lines.

As illustrated in FIG. 1, in normal individuals, lysosomal degradation of GAGs (e.g., heparan sulfate) produces monosaccharides and sulfate. Provided in certain embodiments herein is a process of detecting and/or measuring the accumulation of GAG fragments in cultured primary human fibroblasts from MPS patients. In some instances, and as illustrated in FIG. 2, the GAGs that accumulate in MPS patients are much smaller than normal tissue GAGs and they lack a core protein on their reducing termini. As illustrated in FIG. 3, individuals suffering from MPS (e.g., MPS II, as specifically illustrated in FIG. 3) accumulate GAG fragments. FIG. 4 illustrates the accumulation of GAG in wild type, MPS I and MPS II cells human fibroblasts. In accordance with the processes described herein, GAGs purified from MPS cells or tested cells are tagged with a detectable label (e.g., with a fluorescent label) on free reducing ends of the GAGs and analyzed by a device suitable for detecting the label (e.g., by purification, such as with an HPLC, and detection/measurement of the detectable label). In general, most cellular GAGs of non-MPS cells have a core protein on the reducing end. Therefore, in most instances, the background signal from normal GAGs (i.e., protein bound GAGs) in a sample or GAGs present in non-MPS cells is very low. Because this method detects the number of GAG fragments in the sample (instead of the mass of GAG) it is extremely sensitive. Thus, in some instances, a small 2-fold increase in GAG mass would lead to a >10-fold increase in the number of free reducing ends. In certain embodiments, the source of the GAGs used in any process herein is any source, including a cell. In some embodiments, the cell is any cell where GAG accumulation (e.g., abnormal GAG accumulation) is possible or suspected. In specific embodiments, the processes described herein have high sensitivity for GAGs, particularly GAGs that are non-protein bound. In certain embodiments, GAGs detected according to any process described herein is from, e.g., brain tissue or cells, liver tissue or cells, kidney tissue or cells, or the like (e.g., in tissue or cells suspected of having abnormal GAG accumulation).

In some embodiments, a process of detecting glycosaminoglycans according to a process provided herein comprises: characterizing a population of glycosaminoglycans that have been tagged with a detectable label to the glycosaminoglycan (e.g., at the reducing end). In various embodiments, any suitable detectable label is utilized. Detectable labels are attached to the glycosaminoglycan (e.g., at the reducing end) using any suitable technique. In some embodiments, suitable techniques include contacting the glycosaminoglycan with a detectable label comprising a moiety that forms a covalent and/or non-covalent bond with the glycosaminoglycan. In various embodiments, detectable labels include, by way of non-limiting example, mass labels, affinity labels, radiolabels, chromophores, fluorescent labels, or the like. Similarly, such methods are optionally utilized for the detection of other polymeric compounds or glycans.

In certain embodiments, a process of detecting glycosaminoglycans according to a process provided herein comprises: characterizing a population of glycosaminoglycans by subjecting the population of glycosaminoglycans with one or more antibody that binds the glycosaminoglycan (e.g., at the reducing end). In specific embodiments, the antibody or antibodies selectively bind the reducing end of one or more glycosaminoglycan. In some embodiments, the antibody is bound to a detectable label, or the antibody is a detectable label (i.e., it comprises a detectable moiety). Similarly, such methods are optionally utilized for the detection of other polymeric compounds or glycans.

In certain embodiments, the characterization of the population of glycosaminoglycans comprises a characterization of the population of glycosaminoglycans with an analytical device. In specific embodiments, the analytical device comprises a spectrometer that detects and/or measures a detectable label. In more specific embodiments, the spectrometer includes, by way of non-limiting example, one or more of a mass spectrometer, a nuclear magnetic resonance spectrometer, a UV-Vis spectrometer, an IR spectrometer, a fluorimeter, a phosphorimeter, a radiation spectrometer, or the like. In some embodiments, the process comprises displaying or recording the results of the characterization. In certain embodiments, the results are displayed on a display monitor (e.g., a computer monitor, television, PDA, or the like), or print out. In some embodiments, the results are recorded on an electronic medium (e.g., a hard disk drive, magnetic storage drive, optical storage drive or the like; a disk such as a floppy disk, CD, DVD, BLU-ray or the like; a flash memory drive; removable drive or the like).

Provided in some embodiments herein is a process for diagnosing or diagnosing the severity of a disorder associated with abnormal glycosaminoglycan degradation and/or glycosaminoglycan accumulation in an individual, the process comprising:
(d) providing a test sample comprising glycosaminoglycans;
(e) quantifying the glycosaminoglycan end groups of a population of glycosaminoglycans within the test sample; and
(f) displaying or recording a quantification of the population of glycosaminoglycans.

In some embodiments, the glycosaminoglycans (GAGs) present in the test sample include one or more of: chondroitin sulfate and/or one or more different fragment thereof; dermatan sulfate and/or one or more different fragment thereof; heparan sulfate and/or one or more different fragment thereof; keratan sulfate and/or one or more different fragment thereof; hyaluronan and/or one or more different fragment thereof; or a combination thereof. In specific embodiments, the glycosaminoglycans present in the test sample include heparan sulfate and/or one or more different fragment thereof.

In some embodiments, the test sample is a biological sample. In certain embodiments, the test sample is a sample obtained from an incubation of cells with a compound (e.g., to identify compounds effective in modulating biosynthesis of a glycosaminoglycans in general, or any particular glycosaminoglycan, such as heparan sulfate).

In certain embodiments, quantifying glycosaminoglycan end groups of a population of glycosaminoglycans according to any process described herein comprises (i) contacting a glycosaminoglycan containing sample with agents that selectively bind a glycosaminoglycan end group (e.g., reducing end group) of the population of glycosaminoglycans; and (ii) quantifying the amount of glycosaminoglycan end groups (e.g., reducing end groups) bound to the agents. In some embodiments, quantifying a glycosaminoglycan end groups of a population of glycosaminoglycans according to any process described herein comprises (i) tagging a representative portion of the glycosaminoglycan end groups (e.g., reducing end groups) of the population of glycosaminoglycans with detectable labels; and (ii) quantifying the detectable labels attached to the glycosaminoglycan end groups (e.g., reducing end groups) of the population of glycosaminoglycans.

In some embodiments, prior to contacting the test sample with agents that selectively bind glycosaminoglycan end groups (e.g., a detectable tag), the test sample is subjected to a process of purification. In certain embodiments, a process described herein further comprises subjecting the test sample to purification techniques (e.g., purifying the glycosaminoglycan containing test sample). In specific embodiments, such purification techniques provide a purified test sample that comprises an increased ratio of glycosaminoglycans to other particles and/or compounds (i.e., non-glycosaminoglycan particles and/or compounds) within the test sample; and/or that comprises an increased ratio of a particular glycosaminoglycan or group of glycosaminoglycans to other particles or compounds within the test sample.

Provided in some embodiments herein is a process for detecting glycosaminoglycans in a sample, the process comprising the steps of:

(a) characterizing with an analytical device, within a sample, a population of glycosaminoglycans that have been tagged with a detectable label at the reducing end of the glycosaminoglycan; and (b) displaying or recording a characterization of the population of tagged glycosaminoglycans.

In certain embodiments, a biological sample provided in any process described herein is any suitable biological sample including, by way of non-limiting example, blood, serum, urine, hair, saliva, skin, tissue, cerebrospinal fluid (CSF), or the like. In certain embodiments, processes for detecting glycosaminoglycans in a sample further comprise providing, from the individual, a test biological sample that comprises glycosaminoglycans. In some embodiments, providing a test biological sample from an individual includes obtaining the sample from the individual or obtaining the sample from another source (e.g., from a technician or institution that obtained the sample from the individual).

In some embodiments, a process of detecting glycosaminoglycans in a sample comprises tagging the end (e.g., reducing end) of a representative portion of the glycosaminoglycans in the population of glycosaminoglycans within the biological sample with the detectable label to provide the population of tagged glycosaminoglycans. The ends of the glycosaminoglycans are tagged in any suitable manner, using any suitable detectable label, such as one of those described herein. In some embodiments, characterizing the population of tagged glycosaminoglycans comprises quantifying the tagged glycosaminoglycans. In certain embodiments, characterizing the population of tagged glycosaminoglycans comprises detecting the tagged glycosaminoglycans. In some embodiments, the process further comprises comparing the amount of tagged glycosaminoglycans quantified or detected to a control sample.

In certain embodiments, any process of characterizing a population of tagged glycosaminoglycans described herein includes:

(a) detecting a signal from the tagged glycosaminoglycans in a test sample; and (b) quantifying the intensity of the signal detected.

In some embodiments, the signal is detected with an analytical device (e.g., any analytical device described herein). In certain embodiments, a signal or amount of tagged glycosaminoglycan detected or quantified is compared to a control. In specific embodiments, the control is an amount of tagged glycosaminoglycan, or a signal thereof, wherein the control amount of tagged glycosaminoglycan is known, or the amount of tagged glycosaminoglycan is known to be representative of a certain characteristic (e.g., of a disorder characterized by the abnormal degradation, biosynthesis and/or accumulation of the glycosaminoglycan). In some embodiments, the control sample is or has been treated in a manner substantially similar to the test biological sample.

In some embodiments, the quantification of the signal detected, the amount of tagged glycosaminoglycan, or a recording or display of either of such quantifications are compared to a control. In certain embodiments, the control is obtained in (e.g., from a control sample) a similar manner from a known sample (e.g., having a known amount of glycosaminoglycans, a known amount of one or more glycosaminoglycans, having come from a known source, such as an individual suffering from MPS, or an individual not suffering from MPS, or the like).

In some embodiments, one or more different type of glycosaminoglycan (GAG) in a sample are tagged in accordance with any process described herein. In certain embodiments, all glycosaminoglycans tagged in the sample are tagged with the same detectable label. In certain embodiments, characterizing the population of tagged glycosaminoglycans according to any process described herein comprises quantifying the amount of one or more different types of tagged glycosaminoglycan. In various embodiments, the one or more different types of tagged glycosaminoglycan are either cumulatively quantified, or separately and individually quantified. In more specific embodiments, a single type of glycosaminoglycan is individually quantified, when one or more different type of glycosaminoglycan is also tagged (e.g., with a similar or different tag).

In some embodiments, according to any process described herein, glycosaminoglycans, or fragments thereof, of different types are labeled with different detectable labels. In certain embodiments, according to any process described herein, different glycosaminoglycan fragments are labeled with different detectable labels. In various embodiments, the different glycosaminoglycan fragments are of the same or different type of glycosaminoglycan. In certain embodiments, one or more different types of glycosaminoglycan, or fragments thereof, in a sample are detected and/or quantified. In some embodiments, the one or more different types of tagged glycosaminoglycans are one or more different tagged chondroitin sulfate fragments, one or more different tagged dermatan sulfate fragments, one or more different tagged heparan sulfate fragments, one or more different tagged keratan sulfate fragments, one or more different tagged hyaluronan fragments, or a combination thereof. In specific embodiments, the one or more different types of tagged glycosaminoglycan detected and/or quantified is or comprises one or more different tagged heparan sulfate fragments.

Also provided herein is any tagged glycosaminoglycan described herein. In specific embodiments provided herein is a heparan sulfate fragment tagged at the reducing end thereof. For example, a tagged heparan sulfate fragment provided herein comprises the structure: H-(GlcNHR-GlcA/IdoA)$_n$-detectable label or

wherein:

■ is N-acetylglucosamine;

◆ is glucuronic acid;

◇ is iduronic acid; and

▨ is a detectable label.

The symbolic nomenclature used herein follows the "Symbol and Text Nomenclature for Representation of Glycan Structure" as promulgated by the Nomenclature Committee for the Consortium for Functional Glycomics, as amended on October 2007. In some embodiments, GlcNH is glucosamine, and each R is independently H, $SO_3^-$, $SO_3H$, or $COCH_3$. In certain embodiments, each GlcA/IdoA is an uronic acid, each uronic acid being independently selected from D-glucuronic acid and L-iduronic acid. In various embodiments, n is 1-300, 1-100, 1-50, 1-30, 5-300, 5-100, 5-50, 5-30, 10-300, 10-100, 10-30, or the like. Each glucosamine is optionally and independently O-sulfated, e.g., at the 6-position and/or 3-position. Each uronic acid is optionally and independently O-sulfated, e.g., at the 2-position. In some embodiments, provided herein is an analytical sample comprising a population of heparan sulfate fragments tagged at the reducing end thereof. In specific embodiments, the analytical sample is a purified analytical sample comprising a population of heparan sulfate fragments tagged at the reducing end thereof.

In other specific embodiments provided herein is a chondroitin sulfate fragment tagged at the reducing end thereof. For example, a tagged chondroitin sulfate fragment provided herein comprises the structure: H-(GalNAc-GlcA)$_n$-detectable label or

wherein:
- ▨ is N-acetylgalactosamine;
- ◆ is glucuronic acid; and
- ▰ is a detectable label.

In various embodiments, n is 1-300, 1-100, 1-50, 1-30, 5-300, 5-100, 5-50, 5-30, 10-300, 10-100, 10-30, or the like. Each N-acetylgalactosamine is optionally and independently O-sulfated, e.g., at the 6-position and/or 4-position. Each glucuronic acid is optionally and independently O-sulfated, e.g., at the 2-position. In some embodiments, provided herein is an analytical sample comprising a population of chondroitin sulfate fragments tagged at the reducing end thereof. In specific embodiments, the analytical sample is a purified analytical sample comprising a population of chondroitin sulfate fragments tagged at the reducing end thereof.

In other specific embodiments provided herein is a dermatan sulfate fragment tagged at the reducing end thereof. For example, a tagged dermatan sulfate fragment provided herein comprises the structure: H-(GalNAc-IdoA)$_n$-detectable label or

wherein:
- ▨ is N-acetylgalactosamine;
- ◆ is iduronic acid; and
- ▰ is a detectable label.

In various embodiments, n is 1-300, 1-100, 1-50, 1-30, 5-300, 5-100, 5-50, 5-30, 10-300, 10-100, 10-30, or the like. In certain embodiments, the L-iduronic acid of one or more disaccharide subunit (i.e., n-subunit) is optionally and independently substituted with a D-glucuronic acid. Each N-acetylgalactosamine is optionally and independently O-sulfated, e.g., at the 6-position and/or 4-position. Each glucuronic acid is optionally and independently O-sulfated, e.g., at the 2-position. In some embodiments, provided herein is an analytical sample comprising a population of dermatan sulfate fragments tagged at the reducing end thereof. In specific embodiments, the analytical sample is a purified analytical sample comprising a population of dermatan sulfate fragments tagged at the reducing end thereof.

In other specific embodiments provided herein is a keratan sulfate fragment tagged at the reducing end thereof. For example, a tagged keratan sulfate fragment provided herein comprises the structure: H-(GlcNAc-Gal)$_n$-detectable label or

wherein:
- ▰ is N-acetylglucosamine;
- ○ is galactose; and
- ▰ is a detectable label.

In various embodiments, n is 1-300, 1-100, 1-50, 1-30, 5-300, 5-100, 5-50, 5-30, 10-300, 10-100, 10-30, or the like.

Each N-acetylglucosamine is optionally and independently O-sulfated, e.g., at the 6-position. In some embodiments, provided herein is an analytical sample comprising a population of keratan sulfate fragments tagged at the reducing end thereof. In specific embodiments, the analytical sample is a purified analytical sample comprising a population of keratan sulfate fragments tagged at the reducing end thereof.

In other specific embodiments provided herein is a hyaluronan tagged at the reducing end thereof. For example, a tagged hyaluronan fragment provided herein comprises the structure: H-(GluNAc-GlcA)$_n$-detectable label or

wherein:
- ▰ is N-acetylglucosamine;
- ◆ is glucuronic acid; and
- ▰ is a detectable label.

In various embodiments, n is 1-300, 1-100, 1-50, 1-30, 5-300, 5-100, 5-50, 5-30, 10-300, 10-100, 10-30, or the like. In some embodiments, provided herein is an analytical sample comprising a population of hyaluronan fragments tagged at the reducing end thereof. In specific embodiments, the analytical sample is a purified analytical sample comprising a population of hyaluronan fragments tagged at the reducing end thereof.

Diagnostics

In some embodiments, processes described herein for detecting and/or quantifying glycosaminoglycans in a sample are used in a process of diagnosing an individual with a disorder associated with the abnormal degradation, biosynthesis and/or accumulation of glycosaminoglycans (e.g., in cellular lysosomes). In some embodiments, the disorder associated with abnormal degradation, biosynthesis and/or accumulation of glycosaminoglycans includes disorders associated with the abnormal degradation, biosynthesis and/or accumulation of chondroitin sulfate and/or one or more different fragments thereof; dermatan sulfate and/or one or more different fragments thereof; heparan sulfate and/or one or more different fragments thereof; keratan sulfate and/or one or more different fragments thereof; hyaluronan and/or one or more different fragment thereof; or a combination thereof. In specific embodiments, a disorder associated with abnormal degradation, biosynthesis and/or accumulation of glycosaminoglycans is a lysosomal storage disease, such as, mucopolysaccharidosis (MPS). In more specific embodiments, the mucopolysaccharidosis (MPS) is MPS I, MPS II, MPS IIIA, MPS IIIB, MPS IIIC, MPS IIID, MPS IVA, MPS IVB, MPS VI, MPS VII, MPS IX or a combination thereof.

Provided in certain embodiments herein is a process for diagnosing or diagnosing the severity of a disorder associated with abnormal glycosaminoglycan degradation in an individual, the process comprising:
a. providing a test biological sample from the individual, the biological sample comprising glycosaminoglycans; and
b. characterizing or quantifying the glycosaminoglycan end groups (e.g., reducing end groups) of a population of glycosaminoglycans within the test biological sample.

Figure 5B:
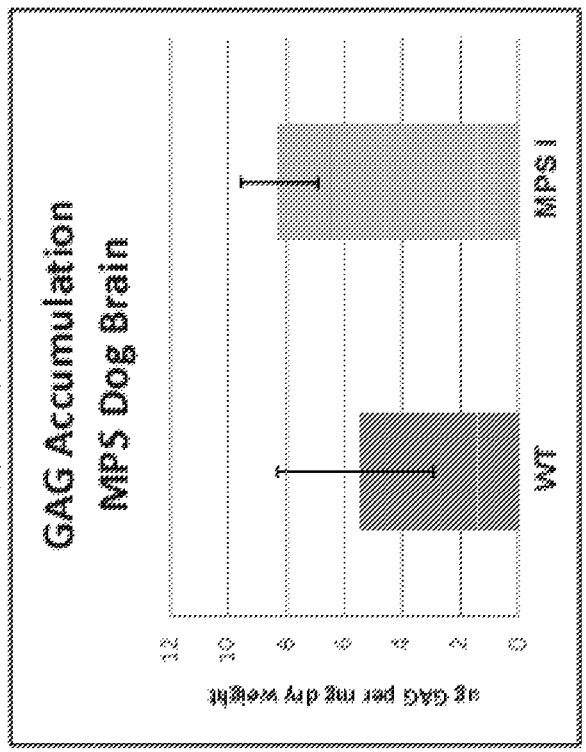
FIG. 5B illustrates GAG accumulation in MPS dog brains, as measured by end group detection according to a method described herein.
Figure 5A:
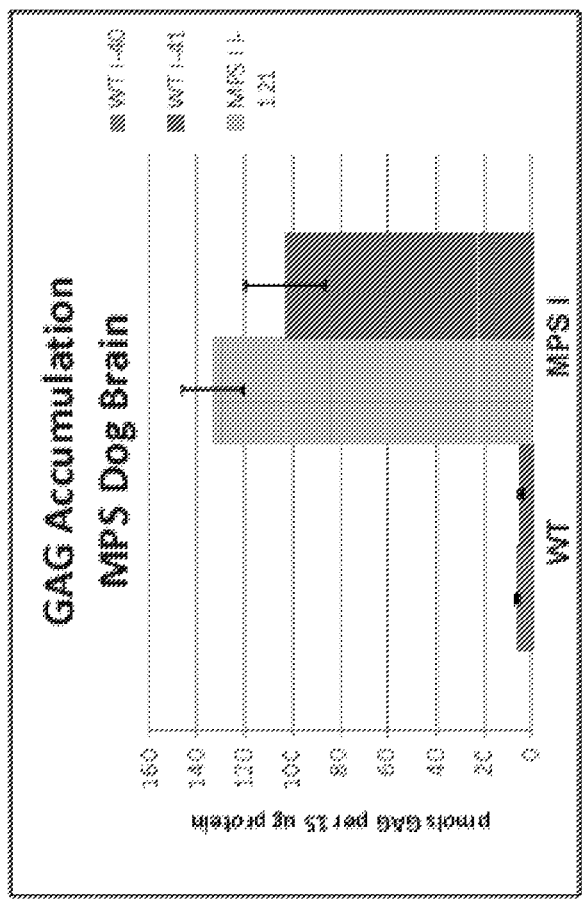
FIG. 5A illustrates GAG accumulation in MPS dog brains, as measured by amount of GAG.
Figure 6:
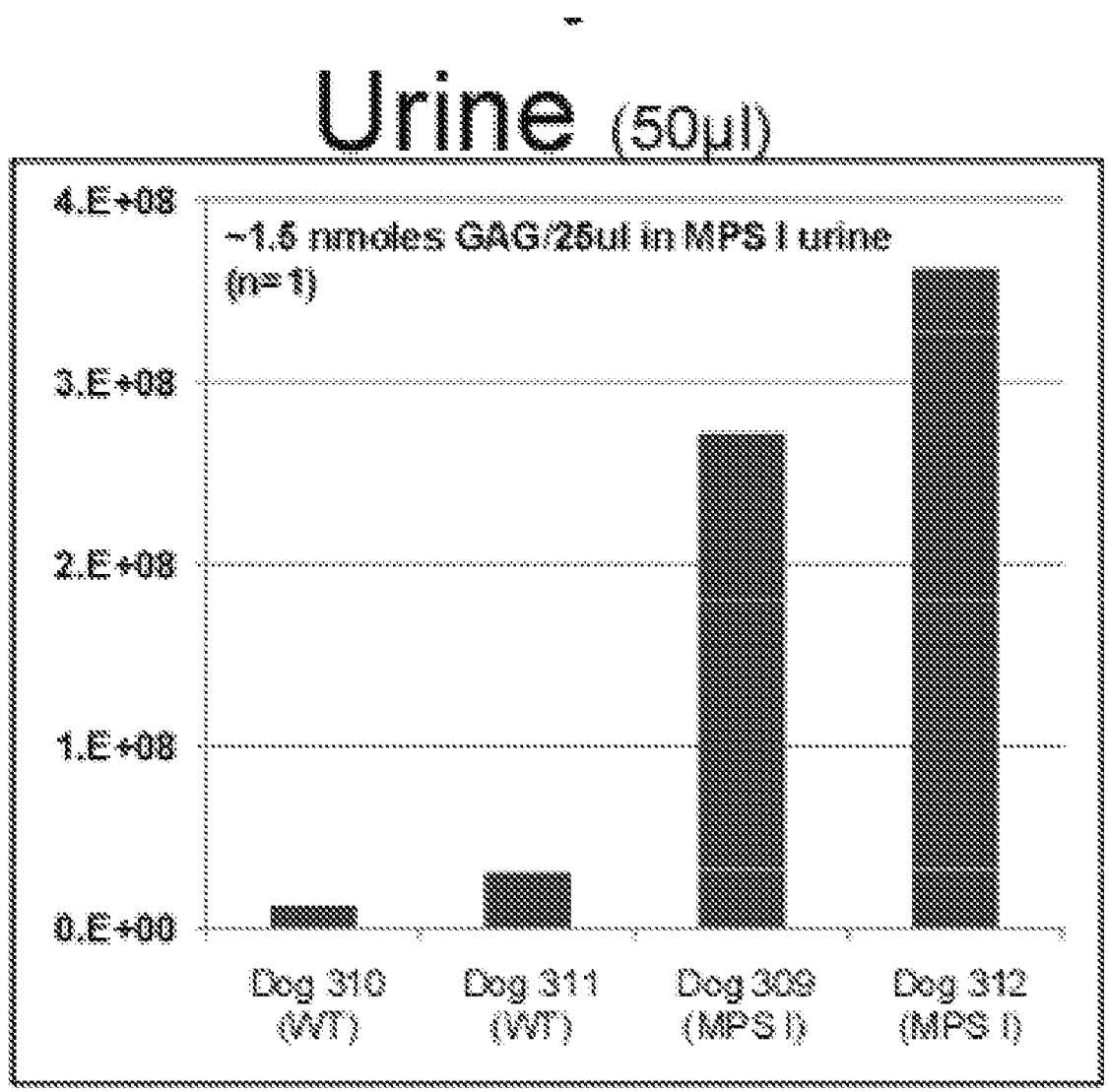
FIG. 6 illustrates GAG accumulation in MPS dog urine.
Figure 7:
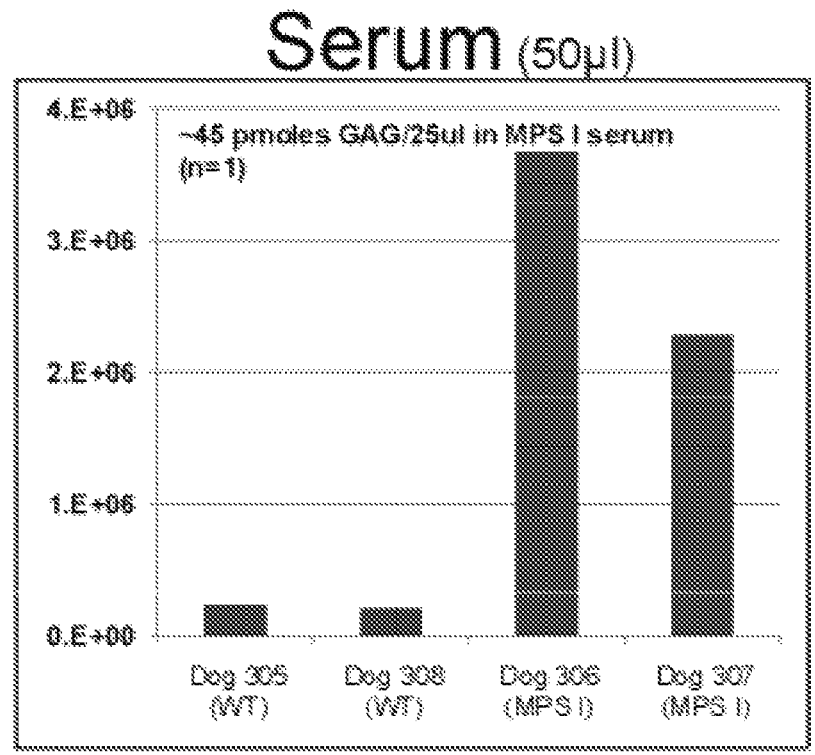
FIG. 7 illustrates GAG accumulation in MPS dog serum.
Figure 8:
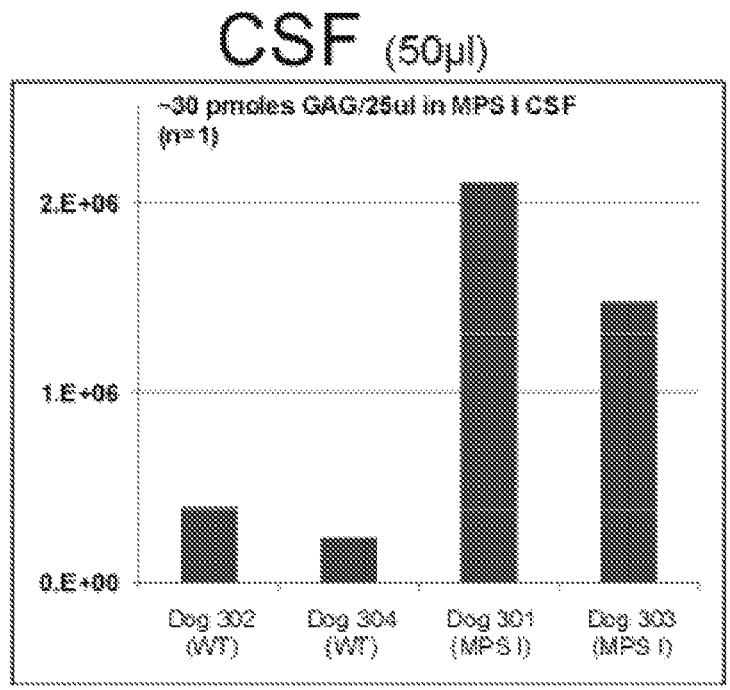
FIG. 8 illustrates GAG accumulation in MPS dog CSF.

In certain embodiments, a biological sample provided in any process described herein is any suitable biological sample including, by way of non-limiting example, blood, serum, urine, hair, saliva, skin, tissue, cerebrospinal fluid (CSF), or the like. In certain embodiments, processes for detecting glycosaminoglycans in a sample further comprise providing, from the individual, a test biological sample that comprises glycosaminoglycans. In some embodiments, providing a test biological sample from an individual includes obtaining the sample from the individual or obtaining the sample from another source (e.g., from a technician or institution that obtained the sample from the individual). FIG. 5 illustrates the benefits of processes described herein as compared to conventional methods of detecting the amount of GAG in a biological sample. FIGS. 6, 7, and 8 illustrate that these processes are effective in detecting lysosomal storage diseases (e.g., MPS) in biological samples (e.g., in dogs) from various sources including, e.g., urine, serum and cerebrospinal fluid (CSF), respectively.

In some embodiments, the end groups (e.g., reducing end groups) are directly quantified according to any process described herein, e.g., by a quantitative nuclear magnetic resonance analysis; or are indirectly quantified. In certain embodiments, the end groups (e.g., reducing end groups) are tagged with a detectable label and the detectable label is detected and/or quantified. Detectable labels include, by way of non-limiting example, mass labels, antibodies, affinity labels, radiolabels, chromophores, fluorescent labels, or the like.

In some embodiments, an individual of any process for diagnosing abnormal glycosaminoglycan accumulation, biosynthesis, and/or degradation or a method of treatment described herein is a human infant (e.g., a newborn) or fetus. In certain embodiments, the diagnostic method is utilized to diagnose severity of a disease, or a carrier of a disease. In some embodiments, diagnosis of one or more carrier parent is optionally utilized to make a progeny risk assessment (e.g., likelihood of a child being a carrier for or having a disease state).

In certain embodiments, a process described herein further comprises displaying or recording a characterization or quantification of a population of glycosaminoglycans.

In some embodiments, the population of glycosaminoglycans (GAGs) present in the test biological sample includes one or more of: chondroitin sulfate and/or one or more different fragments thereof; dermatan sulfate and/or one or more different fragments thereof; heparan sulfate and/or one or more different fragments thereof; keratan sulfate and/or one or more different fragments thereof; hyaluronan and/or one or more different fragments thereof; or a combination thereof. In specific embodiments, the glycosaminoglycans present in the test sample include heparan sulfate and/or one or more different fragments thereof. In specific embodiments, the population of glycosaminoglycans (GAGs) comprises heparan sulfate, one or more heparan sulfate fragments, or a combination thereof.

In some embodiments, the step of quantifying the glycosaminoglycan end groups of a population of glycosaminoglycans comprises (i) tagging a representative portion of the glycosaminoglycan end groups of the population of glycosaminoglycans with detectable labels; and (ii) quantifying the detectable labels attached to the glycosaminoglycan end groups of the population of glycosaminoglycans. In certain embodiments, the step of quantifying the glycosaminoglycan end groups of a population of glycosaminoglycans comprises (i) contacting the test biological sample with agents that selectively bind a glycosaminoglycan end group of the population of glycosaminoglycans; and (ii) quantifying the amount of glycosaminoglycan end groups bound to the agents. Methods of tagging glycosaminoglycan end groups and detectable labels attached to glycosaminoglycan end groups are described herein.

Provided in some embodiments herein is a process for diagnosing or diagnosing the severity of a disorder associated with abnormal glycosaminoglycan degradation in an individual, the process comprising characterizing (e.g., with an analytical device), within a test biological sample from the individual, a population of glycosaminoglycans that have been tagged with a detectable label at the reducing end of the glycosaminoglycan. In more specific embodiments, the characterization is displayed or regarded. In further or alternative embodiments, a process for diagnosing or diagnosing the severity of a disorder associated with abnormal glycosaminoglycan degradation in an individual comprises providing, from the individual, a test biological sample that comprises glycosaminoglycans. In further or alternative embodiments, a process for diagnosing or diagnosing the severity of a disorder associated with abnormal glycosaminoglycan degradation in an individual comprises tagging the reducing end of a representative portion of the glycosaminoglycans in the population of glycosaminoglycans within the biological sample with the detectable label to provide the population of tagged glycosaminoglycans.

In certain embodiments, characterization of the population of tagged glycosaminoglycans comprises quantifying the tagged glycosaminoglycans. In specific embodiments, characterizing the population of tagged glycosaminoglycans includes: detecting a signal from the tagged glycosaminoglycans in the test biological sample and optionally quantifying the intensity of the signal. In further embodiments, the process further comprises comparing the quantified signal intensity in the test biological sample with a quantified signal intensity from tagged glycosaminoglycans in a control biological sample that has been treated in a manner substantially similar to the test biological sample. Tagged glycosaminoglycans are optionally quantified in any suitable manner including through the use of, by way of non-limiting example, mass spectrometry techniques, a nuclear magnetic resonance spectrometry techniques, a UV-Vis spectrometry techniques, an IR spectrometry techniques, fluorometry techniques, a phosphorimetry techniques, a radiation spectrometry techniques, or the like.

Determination of whether or not an individual from whom a test biological sample has been obtained is to be diagnosed with a disorder associated with abnormal degradation, biosynthesis and/or accumulation of glycosaminoglycans (or any one or more specific glycosaminoglycan) is achieved in any suitable manner. For example, in some embodiments, characterization of the glycosaminoglycan end groups (e.g., tagged end groups) of the test biological sample is compared to a standard database or to the results obtained from a control sample subjected to substantially similar conditions as the test biological sample. In certain instances, a standard database can comprise data that was obtained from a control sample that was subjected to substantially similar conditions as well. In some embodiments, the control biological sample is a similar type of sample obtained from an individual that suffers from a disorder associated with abnormal glycosaminoglycan degradation, biosynthesis and/or accumulation (e.g., mucopolysaccharidosis). In more specific embodiments, the individual suffers from MPS I, MPS II, MPS IIIA, MPS IIIB, MPS IIIC, MPS IIID, MPS IVA, MPS IVB, MPS VI, MPS VII, MPS IX or a combination thereof. In other embodiments, the control biological sample is a similar type of sample obtained from an individual that does not suffer from a disorder associated with abnormal glycosaminoglycan degradation, biosynthesis and/or accumulation (e.g., mucopolysaccharidosis). In some embodiments, a control sample is a sample taken from the same individual prior to treatment with an agent known to treat disorders associated with abnormal glycosaminoglycan biosynthesis and/or accumulation.

According to any process herein, characterizing a population of tagged glycosaminoglycans includes, in some embodiments, detecting and/or quantifying different types of tagged glycosaminoglycans within the population of tagged glycosaminoglycans. In some embodiments, the one or more different types of tagged glycosaminoglycans are one or more different tagged heparan sulfate fragments. In certain embodiments, the one or more different types of tagged glycosaminoglycans are one or more different tagged chondroitin sulfate fragments, one or more different tagged dermatan sulfate fragments, one or more different tagged heparan sulfate fragments, one or more different tagged keratan sulfate fragments, one or more different tagged hyaluronan fragments, or a combination thereof.

In some embodiments, characterization of the population of tagged glycosaminoglycans comprises comparing the amount of one or more of the different types of tagged glycosaminoglycans to an amount of one or more of the different types of tagged glycosaminoglycans of a control biological sample (e.g., a sample that has been treated in a manner substantially similar to the test biological sample, as discussed above).

In certain embodiments, a process described herein comprises collecting the glycosaminoglycans from the test biological sample prior to tagging the reducing end of the glycosaminoglycans (e.g., purifying the test and/or control sample prior to tagging the reducing end of the glycosaminoglycan). In some embodiments, the glycosaminoglycan is removed by the proteoglycan by protease digestion and the reducing terminus formed when contacted with a xylosidase.

In some embodiments, severity of a disorder associated with the abnormal degradation, biosynthesis and/or accumulation of glycosaminoglycans is determined in any suitable manner. In some embodiments, the severity of the disorder is determined by using the quantified signal intensity in the test biological sample relative to the quantified signal intensity in the control biological sample.

In certain embodiments, a diagnostic method described herein is utilized to diagnose the presence of and/or severity of an MPS disorder in an individual suffering from symptoms associated with MPS, an individual suspected of suffering from MPS, and/or an individual diagnosed with MPS. In other embodiments, a diagnostic methods described herein is used as a screen for newborn individuals (e.g., humans). Such a use is extremely advantageous because it allows individuals with MPS to be diagnosed early. Early diagnosis of MPS potentially allows for early treatment of MPS, which allows for limited GAG storage in the individual, which otherwise builds up progressively over time.

Detectable Labels

In the various embodiments of any process or method described herein, any suitable detectable label is optionally utilized. In some embodiments, detectable labels useful in the processes or methods described herein include, by way of non-limiting example, mass labels, antibodies, affinity labels, radiolabels, chromophores, fluorescent labels, or the like.

Fluorescent labels suitable for use in various embodiments herein include, by way of non-limiting example, 2-aminopyridine (2-AP), 2-aminobenzoic acid (2-AA), 2-aminobenzamide (2-AB), 2-aminoacridone (AMAC), p-aminobenzoic acid ethyl ester (ABEE), p-aminobenzonitrile (ABN), 2-amino-6-cyanoethylpyridine (ACP), 7-amino-4-methylcoumarine (AMC), 8-aminonaphthalene-1,3,6-trisulfate (ANTS), 7-aminonaphthalene-1,3-disulfide (ANDS), and 8-aminopyrene-1,3,6-trisulfate (APTS), or the like. The fluorescent labels can be attached by reductive amination with the fluorescent label and sodium cyanoborohydride or the like.

Mass labels suitable for use in various embodiments herein include, by way of non-limiting example, D-2-anthranilic acid, D-2-aminopyridine, D-methyl iodide, $^{13}C$ methyl iodide, deuterated-pyridyl-amine, D-biotin or the like. The mass labels can be attached by permethylation or reductive amination by any known method.

Affinity labels suitable for use in various embodiments herein include, by way of non-limiting example, biotin and derivatives, or the like.

Radio labels suitable for use in various embodiments herein include, by way of non-limiting example, sodium borotritide ($NaB^3H_4$), or the like.

Chromophores suitable for use in various embodiments herein include, by way of non-limiting example, 4-amino-1, 1'-azobenzene, 4'-N,N-dimethylamino-4-aminoazobenzene, aminoazobenzene, diaminoazobenzene, Direct Red 16, CI Acid Red 57, CI Acid Blue 45, CI Acid Blue 22, CL Mordant Brown 13, CI Direct Orange 75, or the like. The chromophores may be labeled by any known method, such as reductive amination with the chromophore and sodium cyanoborohydride.

In some embodiments, the detectable label is an antibody, the antibody. In specific embodiments, the antibody is attached to a detectable compound, such as mass labels, radiolabels, chromophores, fluorescent labels, or the like. In some embodiments, antibodies are themselves detected and/or are detectable in various manners, e.g., as a chromophore, a fluorophore, or the like; or with a probe (e.g., using dot blot techniques, immune-detection techniques, or the like).

Purification Processes

In some embodiments, the processes described herein comprise further treatment steps of the test and/or control samples. For example, in some embodiments, the samples are homogenized and/or purified. In specific embodiments homogenization is achieved in any suitable manner including, by way of non-limiting example, with a basic solution (e.g., 0.1 N NaOH), sonication, tissue grinding, or other chemical agents).

In certain embodiments, samples, including test samples and/or control samples, described herein are optionally purified prior to glycosaminoglycan tagging and/or characterization. Test samples and/or control samples (i.e., one or more or all of the glycans found therein) are optionally purified using any suitable purification technique. Test samples and/or control samples are optionally purified at any suitable point in a process described herein, including before or after tagging of the glycans founds within the sample. In certain embodiments, purification techniques include electrophoresis, chromatography, column chromatography, gas chromatography, high performance liquid chromatography, thin layer chromatography, ion exchange chromatography, gel chromatography, molecular sieve chromatography, affinity chromatography, exclusion, filtration, precipitation, osmosis, recrystallization, fluorous phase purification, distillation, extraction, chromatofocusing, or the like.

For example, the biological sample (cells, tissue, blood, serum, cerebrospinal fluid, or the like) is homogenized and solubilized in a basic or acidic composition, such as aqueous (e.g., 0.1-1.0 N, 0.1 N, 0.2 N, 0.3 N, 0.4 N, 0.5 N, 0.6 N, 0.7 N, 0.8 N, 0.9 N, or 1 N NaOH or acetic acid). The biological sample is then optionally neturalized (e.g., with acetic acid or NaOH). Next a small sample is taken to measure protein content of the sample using standard methods. Optionally protease (e.g., 0.01-0.5 mg/mL, 0.01 mg/mL, 0.02 mg/mL, 0.03 mg/mL, 0.04 mg/mL, 0.05 mg/mL, 0.1 mg/mL, 0.14 mg/mL, 0.17 mg/mL, 0.2 mg/mL, 0.23 mg/mL, 0.25 mg/mL, 0.27 mg/mL, 0.3 mg/mL, 0.4 mg/mL, 0.5 mg/mL) (exemplary protease include, by way of non-limiting example, trypsin, chymotrypsin, pepsin, pronase, papain, or elastase) is added and the sample is treated in 0.1-0.5 M (e.g., e.g., 0.1 M, 0.16 M, 0.23 M, 0.32 M, 0.39 M, 0.44 M, or 0.5 M) NaCl, 0.01-0.1 M (e.g., 0.01 M, 0.02 M, 0.04 M, 0.06 M, 0.08 M, 0.1 M) NaOAc, at pH 5.5-7.5 (e.g., 5.5, 6.0, 6.5, 7.0, or 7.5) and 25-40 C (e.g., 25 C, 30 C, 35 C, or 40 C) for 1-24 hours (e.g., 1 h, 2 h, 4 h, 6 h, 8 h, 12 h, 18 h, 24 h). In some embodiments, the sample is diluted (e.g., to reduce the ionic strength). In certain embodiments, a sample is then loaded onto an ion exchange column (e.g., in 5-100 mM NaOAc (e.g., 5 mM, 10 mM, 20 mM, 30 mM, 40 mM, 50 mM, 60 mM, 70 mM, 75 mM, 80 mM, 90 mM, 95 mM, 100 mM) pH 5-7 (e.g., 5.5, 6.0, 6.5, 7.0) with 0-300 mM NaCl (e.g., 5 mM, 10 mM, 20 mM, 30 mM, 40 mM, 50 mM, 60 mM, 70 mM, 75 mM, 80 mM, 90 mM, 95 mM, 100 mM, 150 mM, 200 mM, 250 mM, 300 mM)). In some embodiments, after washing, the bound glycosaminoglycans are eluted with a suitable solvent or solvent system (e.g., with 5-100 mM (e.g., 5 mM, 10 mM, 20 mM, 30 mM, 40 mM, 50 mM, 60 mM, 70 mM, 75 mM, 80 mM, 90 mM, 95 mM, 100 mM) NaOAc pH 5-7 (e.g., 5.5, 6.0, 6.5, 7.0) with 0.8-3 M NaCl (e.g., 0.8 M, 1 M, 1.2 M, 1.4 M, 1.6 M, 1.8 M, 2 M, 2.5 M, or 3 M)). In certain embodiments, the eluted glycans are then concentrated and/or desalted (e.g., by ethanol precipitation, size exclusion, or other methods). The purified glycans are optionally dried for further analysis. In some embodiments, e.g., if dried, a dried glycan sample is re-suspended in a suitable liquid (e.g., 2-100 µL (2 µL, 5 µL, 10 µL, 15 µL, 20 µL, 25 µL, 30 µL, 40 µL, 50 µL, 60 µL, 70 µL, 80 µL, 90 µL, or 100 µL) 0.003-0.1 M (e.g., 0.003 M, 0.003 M, 0.03 M, 0.06 M, 0.1 M) 2-aminopyridine (2-AP), 2-aminobenzoic acid (2-AA), 2-aminobenzamide (2-AB), 2-aminoacridone (AMAC), p-aminobenzoic acid ethyl ester (ABEE), p-aminobenzonitrile (ABN), 2-amino-6-cyanoethylpyridine (ACP), 7-amino-4-methylcoumarine (AMC), 8-aminonaphthalene-1,3,6-trisulfate (ANTS), 7-aminonaphthalene-1,3-disulfide (ANDS), and 8-aminopyrene-1,3,6-trisulfate (APTS), Bodipy or the like) and incubated at a suitable temperature for a suitable time (e.g., at room temperature for 1-120 minutes). In certain embodiments, the reaction is then initiated (e.g., with 2-100 µL (e.g., 2 µL, 5 µL, 10 µL, 15 µL, 20 µL, 25 µL, 30 µL, 40 µL, 50 µL, 60 µL, 70 µL, 80 µL, 90 µL, or 100 µL) 1 M NaCNBH$_4$) and the reaction is allowed to proceed at a suitable temperature (e.g., 25-100 C, 25 C, 30 C, 35 C, 40 C, 50 C, 60 C, 70 C, 80 C, 90 C, 100 C).

In some embodiments, glycosaminoglycans, such as heparan sulfate, are naturally found attached to a core protein (together forming a proteoglycan). In some embodiments, provided herein are purification processes of separating glycosaminoglycan fragments (e.g., heparan sulfate fragments) from proteoglycans prior to tagging and processing the glycosaminoglycan fragments for detection. In certain instances, this provides an improved process whereby "noise" from natural glycosaminoglycans are reduced. A similar effect is optionally achieved by tagging the glycosaminoglycan fragments in the presence of the proteoglycans (e.g., without subjecting the sample to conditions that cleave the glycan-protein linkage). In certain embodiments, a purification process used herein is a process that includes a protocol that cleaves a core protein from a glycosaminoglycan (e.g., treatment with a protease, such as a non-specific protease (e.g., Pronase) to cleave the proteins; or by chemical means (beta-elimination chemistry)). In other embodiments, a purification process described herein does not include a protocol that cleaves a glycosaminoglycan from a core protein.

Figure 9:
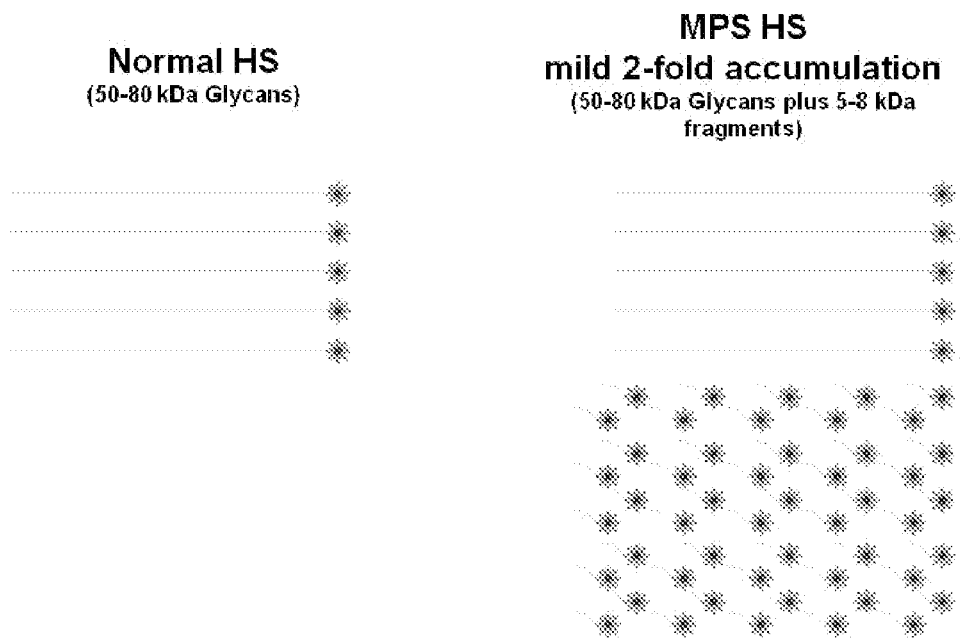
FIG. 9 illustrates a tagged population of glycosaminoglycans (e.g., heparan sulfate and fragments thereof) in a purified sample subjected to cleavage of the glycan-protein linkage, wherein prior to tagging, the sample on the left side was provided from an individual with normal glycosaminoglycan degradation was provided from an individual suffering from a disorder associated with abnormal glycosaminoglycan degradation, biosynthesis, and/or degradation (e.g., abnormal heparan sulfate degradation, biosynthesis, and/or accumulation).
Figure 10:
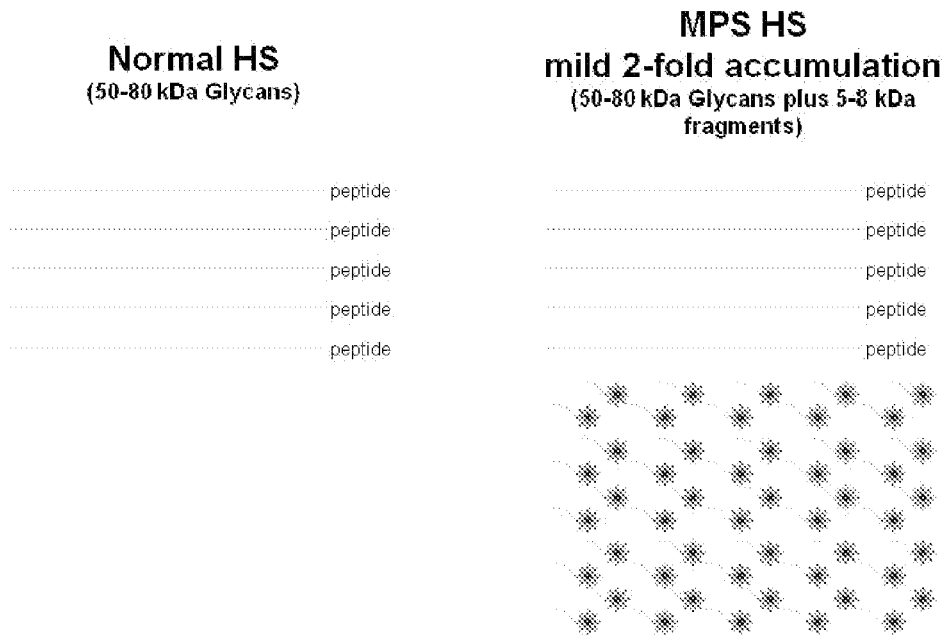
FIG. 10 illustrates a tagged population of glycosaminoglycans (e.g., heparan sulfate and fragments thereof) in a purified sample that is not subjected to cleavage of the glycan-protein linkage, wherein prior to tagging, the sample on the left side was provided from an individual with normal glycosaminoglycan degradation was provided from an individual suffering from a disorder associated with abnormal glycosaminoglycan degradation, biosynthesis, and/or degradation (e.g., abnormal heparan sulfate degradation, biosynthesis, and/or accumulation).

FIG. 9 illustrates the tagged population of glycosaminoglycans (e.g., heparan sulfate and fragments thereof) in a purified sample subjected to cleavage of the glycan-protein linkage, wherein prior to tagging, the sample on the left side was provided from an individual with normal glycosaminoglycan degradation, the sample on the right side was provided from an individual suffering from a disorder associated with abnormal glycosaminoglycan degradation, biosynthesis, and/or degradation (e.g., abnormal heparan sulfate degradation, biosynthesis, and/or accumulation). FIG. 10 illustrates the tagged population of glycosaminoglycans (e.g., heparan sulfate and fragments thereof) in a purified sample that is not subjected to cleavage of the glycan-protein linkage, wherein prior to tagging, the sample on the left side was provided from an individual with normal glycosaminoglycan degradation the sample on the right side was provided from an individual suffering from a disorder associated with abnormal glycosaminoglycan degradation, biosynthesis, and/or degradation (e.g., abnormal heparan sulfate degradation, biosynthesis, and/or accumulation).

Detection Methods

Glycosaminoglycan end groups (e.g., reducing end groups) or detectable labels described herein are detected in processes described herein in any suitable manner.

In certain embodiments, detectable labels are detected and/or quantified according to any process described herein using any technique, particularly any technique suitable for the detectable label utilized. In some embodiments, suitable detection techniques include, by way of non-limiting example, one or more of a mass spectrometer, a nuclear magnetic resonance spectrometer, a UV-Vis spectrometer, an IR spectrometer, a fluorometer, a phosphorimeter, a radiation spectrometer, a thin layer chromatographic technique, or the like. In certain embodiments, any process described herein glycosaminoglycan end groups are optionally directly detected using a suitable technique, such as quantitative nuclear magnetic resonance. Quantitative nuclear magnetic resonance is also optionally utilized to quantify and/or detect the presence of a detectable label.

For analysis, in certain embodiments, the sample prepared such that the unincorporated dye is removed from the free dye and the incorporated dye is measured on a fluorescent plate reader. In various embodiments, the free dye is removed in any suitable manner (e.g., by ion exchange, size exclusion, HILIC, or other suitable methods).

In alternative embodiments, the sample is run on HPLC using an ion exchange resin (such as a Nucleogen 60-7, ProTex DEAE, or Tsk Gel DEAE-NPR) column running at, e.g., 0.1-2, 0.1, 0.2, 0.3, 0.4, 0.5, 0.6, 0.7, 0.8, 0.9, 1, 1.1., 1.2, 1.3, 1.4, 1.5, 1.6, 1.7, 1.8, 1.9, 2 mL/min. In some of such embodiments, the sample is loaded on the column that was equilibrated in a suitable solvent system (e.g., 5 to 100 mM (e.g., 5 mM, 10 mM, 15 mM, 20 mM, 25 mM, 30 mM, 35 mM, 40 mM, 45 mM, 50 mM, 60 mM, 70 mM, 80 mM, 90 mM, 100 mM) sodium acetate pH 4-8 (e.g., 4, 4.5, 5, 5.5, 6, 6.5, 7, 7.5, or 8) running at 0.1-2 mL/min (e.g., 0.1, 0.2, 0.3, 0.4, 0.5, 0.6, 0.7, 0.8, 0.9, 1, 1.1., 1.2, 1.3, 1.4, 1.5, 1.6, 1.7, 1.8, 1.9, 2 mL/min)). In certain embodiments, components of the sample are eluted utilizing a suitable solvent and/or solvent system, and, optionally, a gradient (e.g., a gradient from 0-0.4 M (e.g., 0, 0.1, 0.2, 0.3, 0.4 M) to 0.5-3 M (e.g., 0.5, 1, 1.5, 2, 2.5, 3 M) NaCl is completed and the column is held in NaCl for a suitable period of time, e.g., 1-5 min, 5-10 min, 10-15 min, 15-20 min, 20-25 min, 25-30 min, 1-30 min, or the like). After the optional holding of the final concentration, the eluent may be switched to a second solvent or solvent system (e.g., an alcohol, such as methanol, ethanol, or isopropanol, acetonitrile, water, or the like). The switch to the second solvent system may be over a period of time, e.g., 15 seconds, 30 seconds, 45 seconds, 60 seconds, 2 min, 3 min, or the like. The second solvent system is optionally held for a period of time, such as 1 min, 2 min, 3 min, 4 min, 5 min, 6 min, or the like. Following the second solvent system cycle, the column is optionally restored to initial solvent conditions.

In some embodiments, glycosaminoglycan end groups (e.g., reducing end groups) are tagged with an antibody or probe, which is, in turn quantified using any suitable method (e.g., dot blot techniques, immune detection techniques, or the like).

Figure 11:
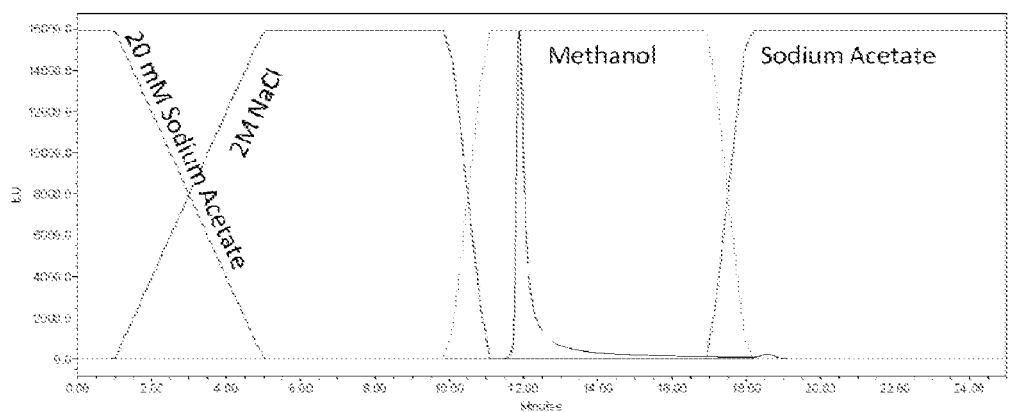
FIG. 11 illustrates fluorescent dye elution.
Figure 15:
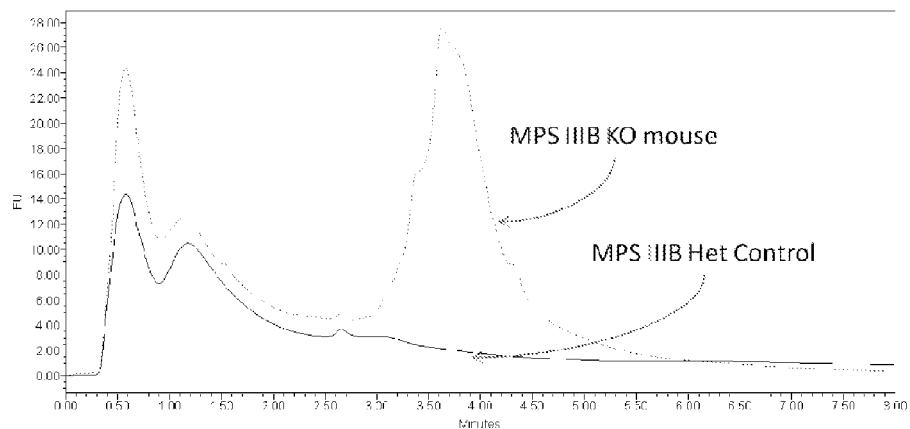
FIG. 15 illustrates the elution of tagged glycosaminoglycans in an MPS sample.
Figure 16:
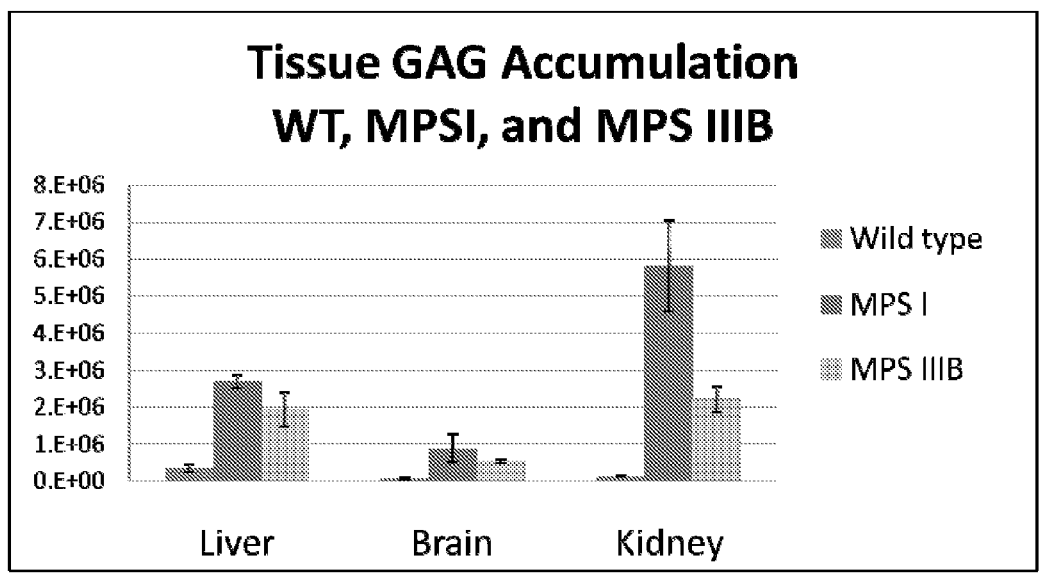
FIG. 16 illustrates the amount GAGs present in tissues from MPS mice, detected following tagging the reducing end of the GAGs with a fluorescent label.
Figure 17:
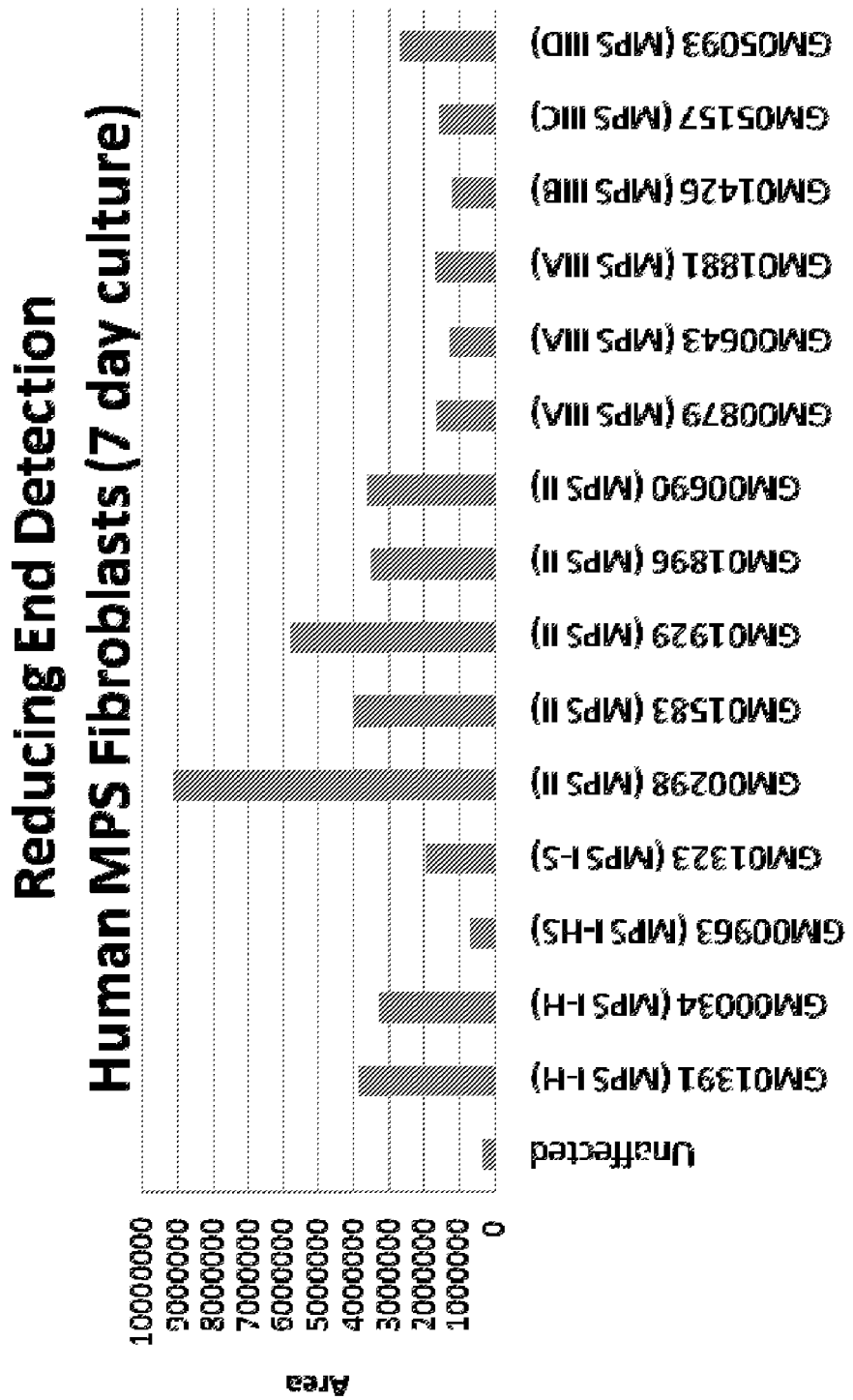
FIG. 17 illustrates the screening of a panel of human MPS cell lines using the methods described herein to detect the severity of accumulation from different human MPS fibroblast cultures. Normal people on the left, show a very low signal, while MPS patients vary dramatically in their level of accumulation. As a result, the methods described herein are useful for identifying patients having MPS, as well as the severity of accumulation.

FIG. 11 illustrates fluorescent dye elution. FIGS. 12-16 illustrate the elution of tagged glycosaminoglycans. FIG. 17 illustrates the screening of a panel of human MPS cell lines using the methods described herein to detect the severity of accumulation from different human MPS fibroblast cultures. Normal people on the left, show a very low signal, while MPS patients vary dramatically in their level of accumulation. As a result, the methods described herein are useful for identifying patients having MPS, as well as the severity of accumulation.

In certain embodiments, detection or measurement of an analytical device provides for diagnosis of a disease, diagnosis of severity of a disease, of efficacy of a therapy, or analysis based on other processes described herein. For example, in some embodiments, absence of a peak or signal (e.g., a peak or signal indicative of the amount of a tagged glycan) indicates that an individual is in a non-diseased state, in remission for a disease state, or undergoing effective therapy for a disease, depending on the circumstances of the diagnosis. In certain embodiments, the presence and/or area of a peak or signal (including, e.g., the presence of a certain signal or peak pattern or fingerprint) is utilized to determine the severity of a disease. In some embodiments, the presence and/or area of a peak or signal is utilized to determine disease, disease severity, disease carrier status or the like, based on a certain threshold value for the disease, disease severity, disease carrier status. Such thresholds are optionally determined in any suitable manner, e.g., by analyzing control samples, such control samples coming from non-diseased individuals, diseased individuals, or the like.

Methods of Treatment

Provided in certain embodiments are methods of treating or monitoring a treatment of disorders associated with the abnormal degradation, biosynthesis and/or accumulation of glycosaminoglycans (GAGs), the methods comprising:
 a. administering an agent for treating MPS (e.g., an agent that modulates glycosaminoglycan biosynthesis, stem cells, enzyme(s) (e.g., in enzyme replacement therapy (ERT)) to an individual in need thereof;
 b. monitoring the accumulation of glycosaminoglycans in the individual using any process described herein for detecting or quantifying the amount of glycosaminoglycans in a sample obtained from the individual.

In certain embodiments, ERT of any process described herein includes administration of, by way of non-limiting example, an enzyme involved in the degradation pathway of a glycosaminoglycan (GAG), such as heparan sulfate. In certain embodiments, ERT of any process described herein includes administration of, by way of non-limiting example, an arylsulfatase B, an N-sulfatase, a glucosamine acetyltransferase, an N-acetylglucosamine 6-transferase, an N-acetylglucosaminidase, an iduronate 2-sulfatase, an iduronidase, an N-sulfatase, a glucosamine acetyltransferase, an N-acetylglucosamine 6-sulfatase, an N-acetylglucosaminidase, a glucuronidase, or a combination thereof.

In specific embodiments, the accumulation of glycosaminoglycans is conducted over a period of time, e.g., over a week, two weeks, a month, two months, three months, six months, a year, or the like. In some embodiments, the detecting method for quantifying the amount of glycosaminoglycans in a sample obtained from an individual comprises characterizing (e.g., with an analytical device), within a test biological sample from the individual, a population of glycosaminoglycans that have been tagged with a detectable label at the reducing end of the glycosaminoglycan. In further embodiments, the process further comprises displaying or recording such a characterization of the population of tagged glycosaminoglycans.

In specific embodiments, the agent that modulates glycosaminoglycan biosynthesis includes glycosaminoglycan accumulation inhibitors, agents that promote glycosaminoglycan degradation, agents that activate enzymes that degrade glycosaminoglycans, agents that inhibit biosynthesis of glycosaminoglycans, or the like. In some embodiments, the agent that modulates glycosaminoglycan biosynthesis is an agent that selectively modulates heparan sulfate biosynthesis, an agent that selectively modulates chondroitin sulfate biosynthesis, an agent that selectively modulates dermatan sulfate biosynthesis, an agent that selectively modulates keratan sulfate biosynthesis, an agent that selectively modulates hyaluronan biosynthesis, or a combination thereof.

Disorders associated with abnormal glycosaminoglycan degradation, biosynthesis, and/or accumulation include any of those described herein (e.g., lysosomal storage disease). In specific embodiments, the lysosomal storage disease is mucopolysaccharidosis (MPS). In some embodiments, the mucopolysaccharidosis (MPS) is MPS I, MPS II, MPS IIIA, MPS IIIB, MPS IIIC, MPS IIID, MPS IVA, MPS IVB, MPS VI, MPS VII, MPS IX, or a combination thereof. In more specific embodiments, the MPS is Hunter's disease. In more specific embodiments, Hunter's disease causes an accumulation of dermatan sulfate and heparan sulfate glycosaminoglycans. In more specific embodiments, the accumulation of dermatan sulfate and heparan sulfate glycosaminoglycans in Hunter's disease is associated with a deficiency in a sulfatase. In other embodiments, the MPS is Hurler's disease. In more specific embodiments, Hurler's disease causes an accumulation of dermatan sulfate and heparan sulfate glycosaminoglycans. In more specific embodiments, the accumulation of dermatan sulfate and heparan sulfate glycosaminoglycans in Hurler's disease is associated with a deficiency in an iduronidase.

In certain embodiments, monitoring the accumulation of glycosaminoglycans in the individual comprises detecting or quantifying the amount of glycosaminoglycans in a sample obtained from the individual (e.g., according to any method described herein) to obtain a first accumulation result (e.g., an initial reading before treatment has begun, or at any other time) and a second accumulation result that is subsequent to obtaining the first result. In some embodiments, the second result is compared to the first result to determine if the treatment is effectively reducing, maintaining, or reducing the rate of increasing glycosaminoglycan (GAG) levels in a substantially identically obtained sample from the individual being treated. In certain embodiments, depending on the difference between the first and second results, the treatment can be altered, e.g., to increase or decrease the amount of agent administered; to substitute the therapeutic agent with an alternative therapeutic agent; or the like. In certain embodiments, the dose of the therapeutic agent is decreased to a maintenance level (e.g., if the GAG level has been reduced sufficiently); further monitoring of GAG levels is optional in such situation, e.g., to ensure that reduced or maintained levels of GAG are achieved.

Figure 18A:
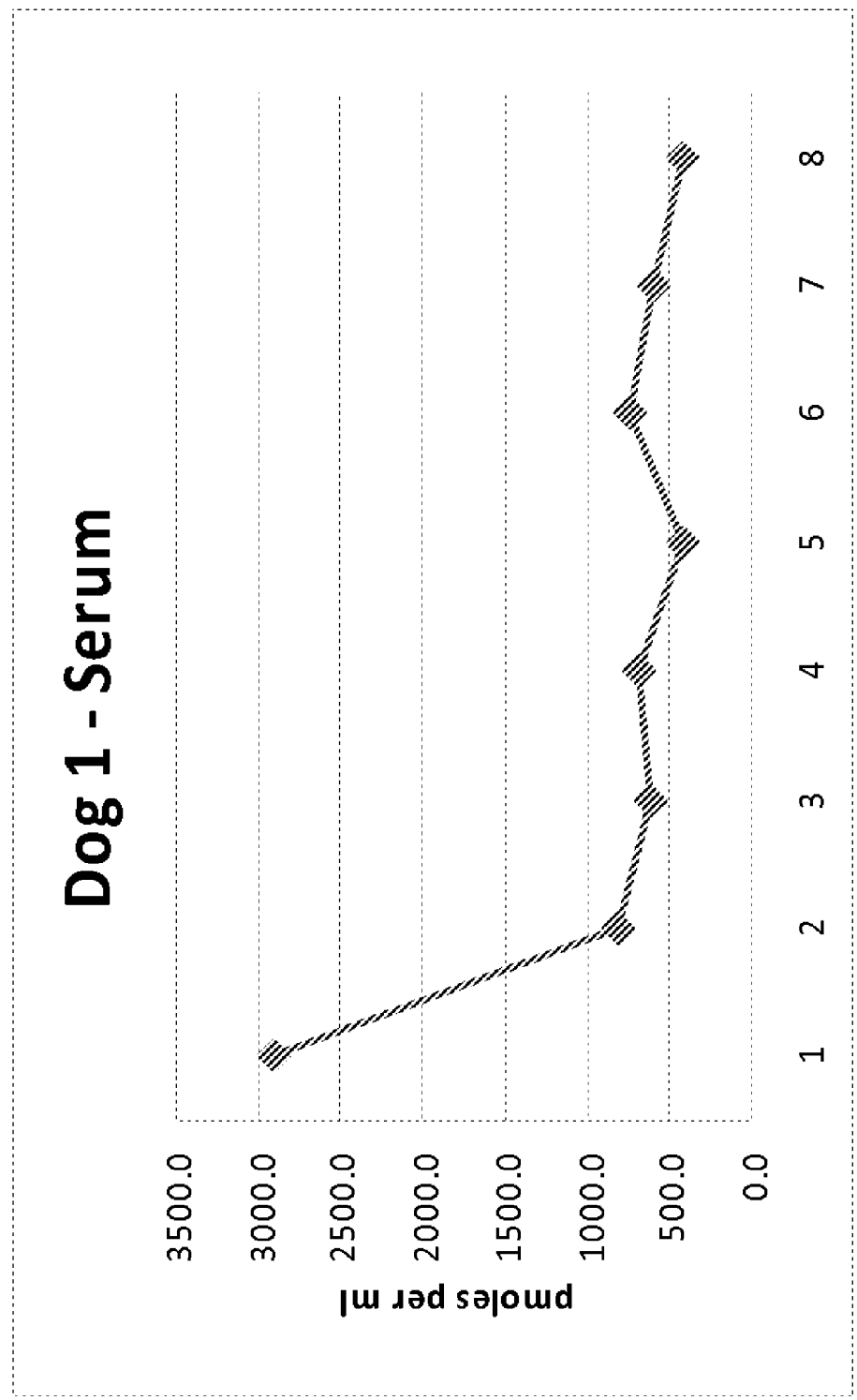
FIG. 18A illustrates monitoring of therapy in an individual by administration of an agent useful for treating MPS in serum samples.
Figure 18B:
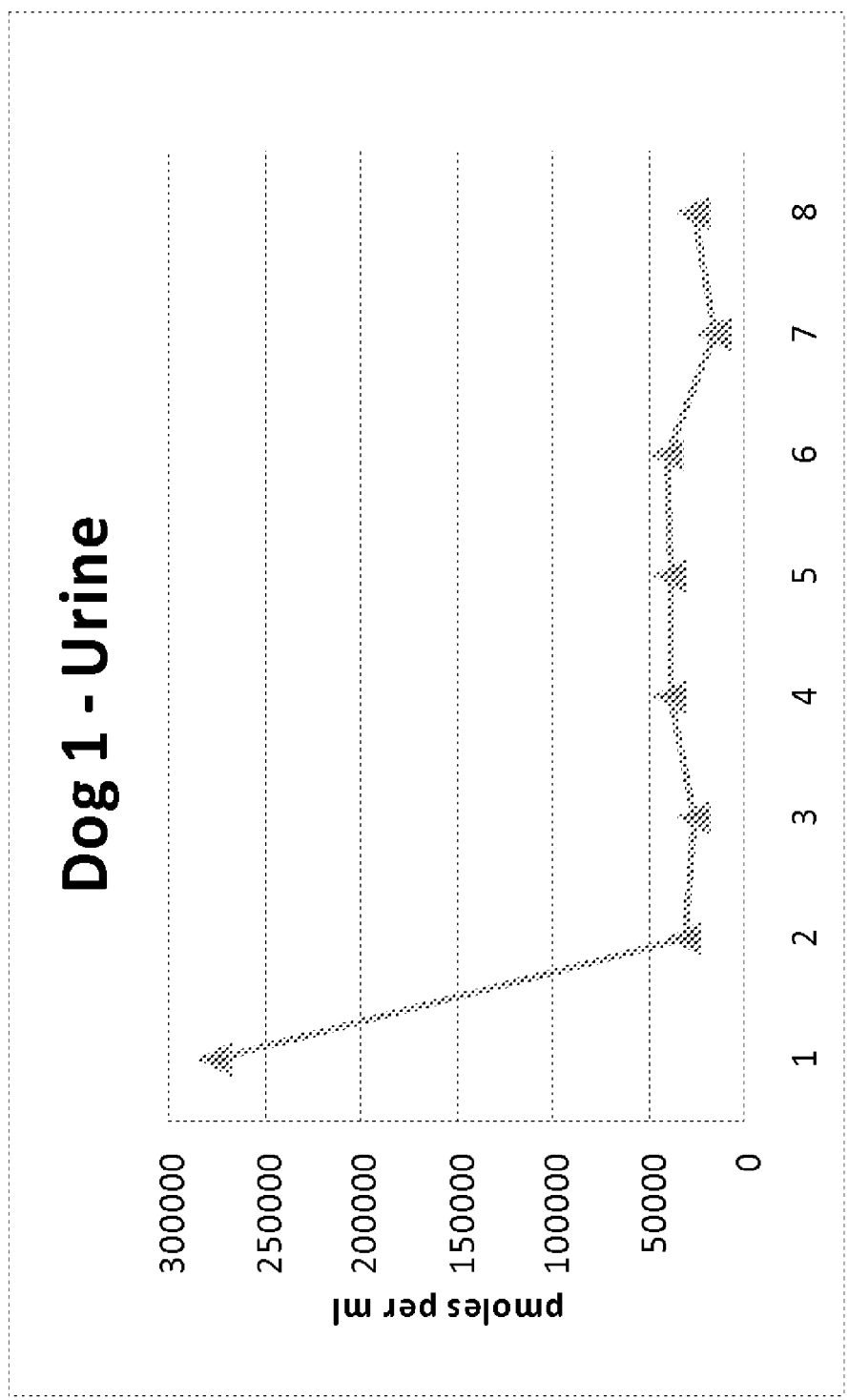
FIG. 18B illustrates monitoring of therapy in an individual by administration of an agent useful for treating MPS in urine samples.
Figure 19A:
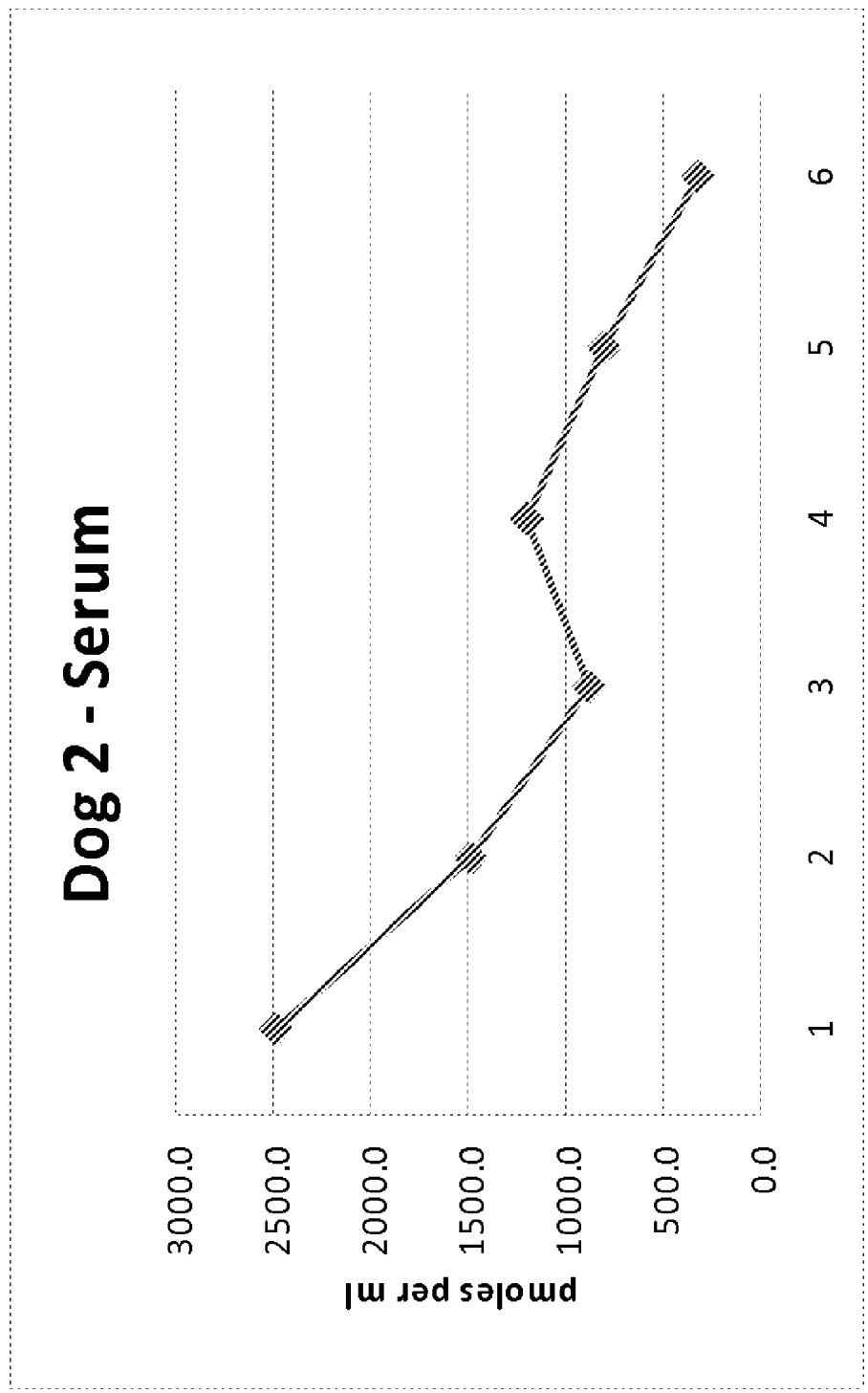
FIG. 19A illustrates monitoring of therapy in an individual by administration of an agent useful for treating MPS in serum samples.
Figure 19B:
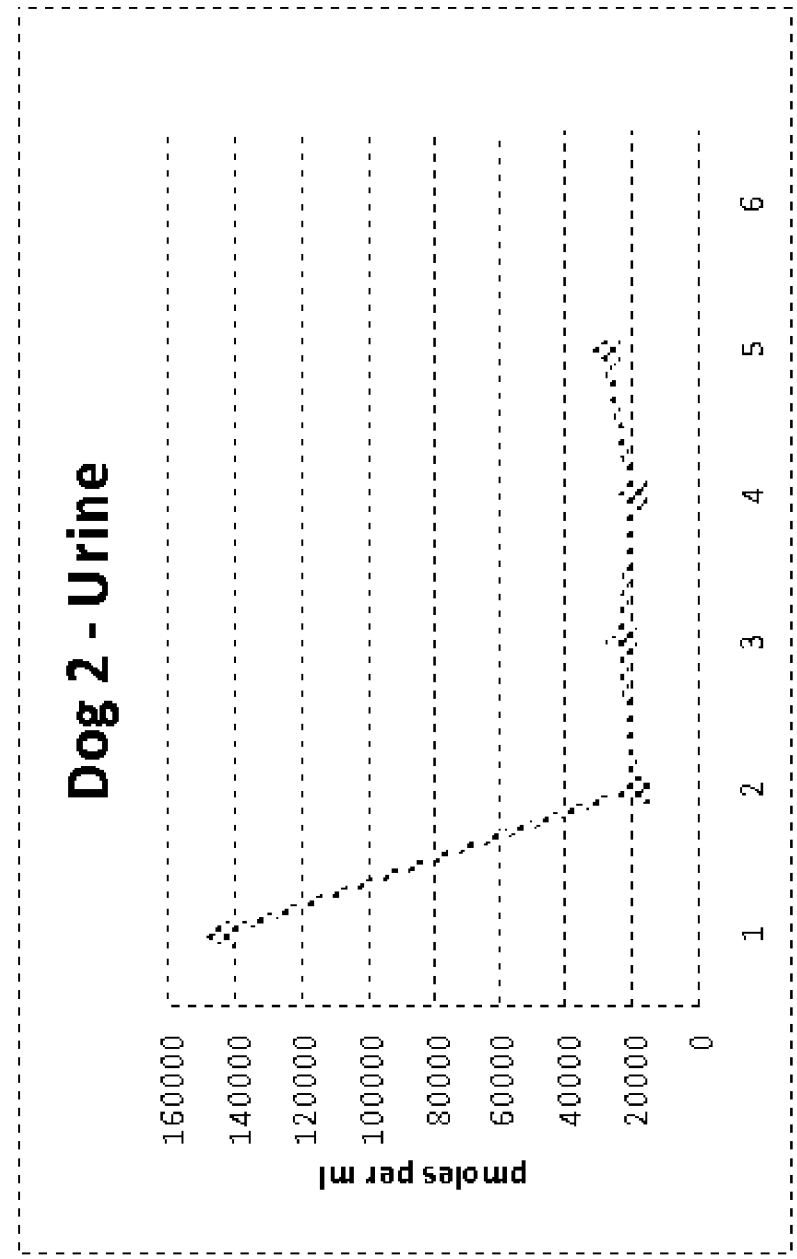
FIG. 19B illustrates monitoring of therapy in an individual by administration of an agent useful for treating MPS in urine samples.
Figure 20A:
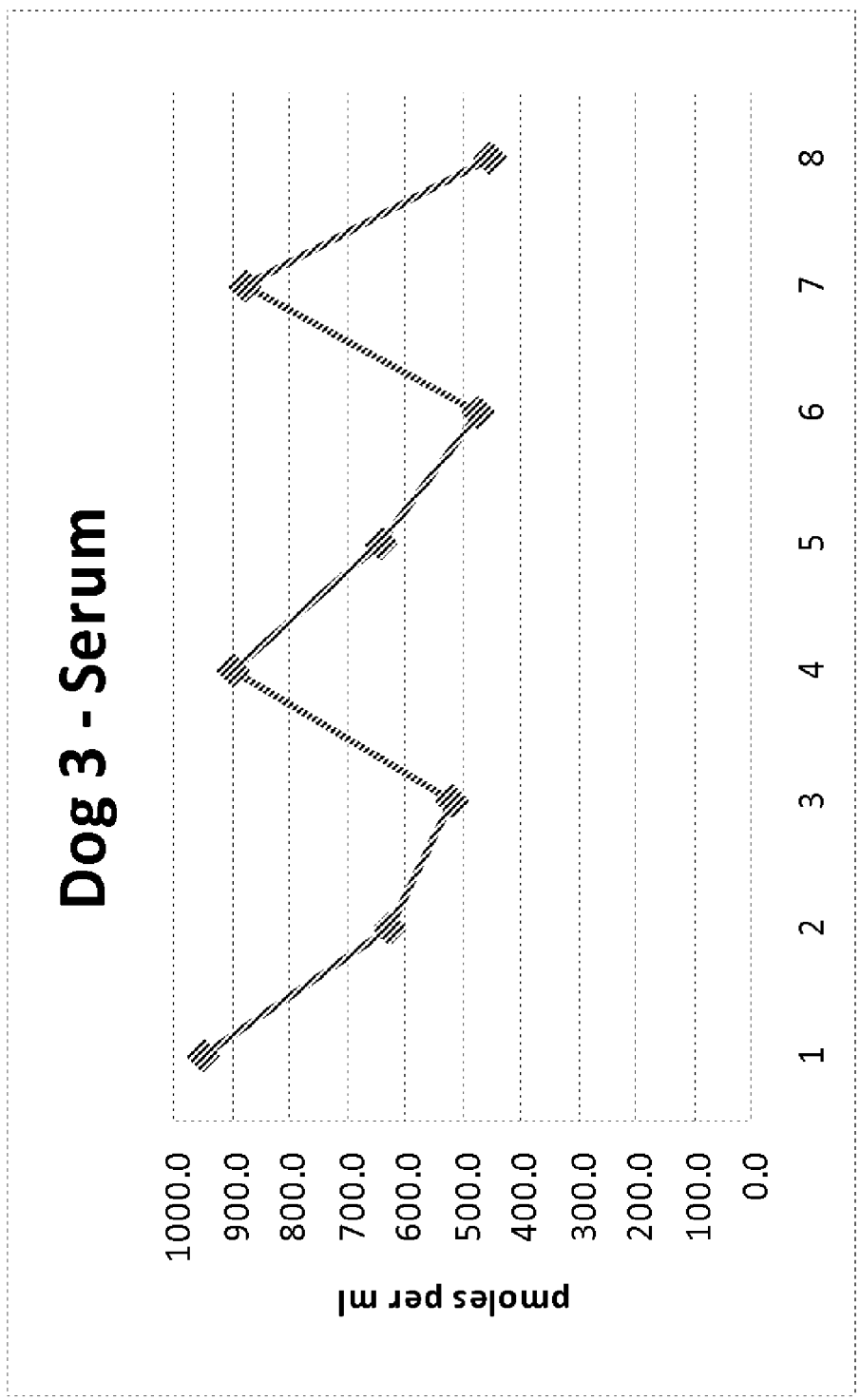
FIG. 20A illustrates monitoring of therapy in an individual by administration of an agent useful for treating MPS in serum samples.
Figure 20B:
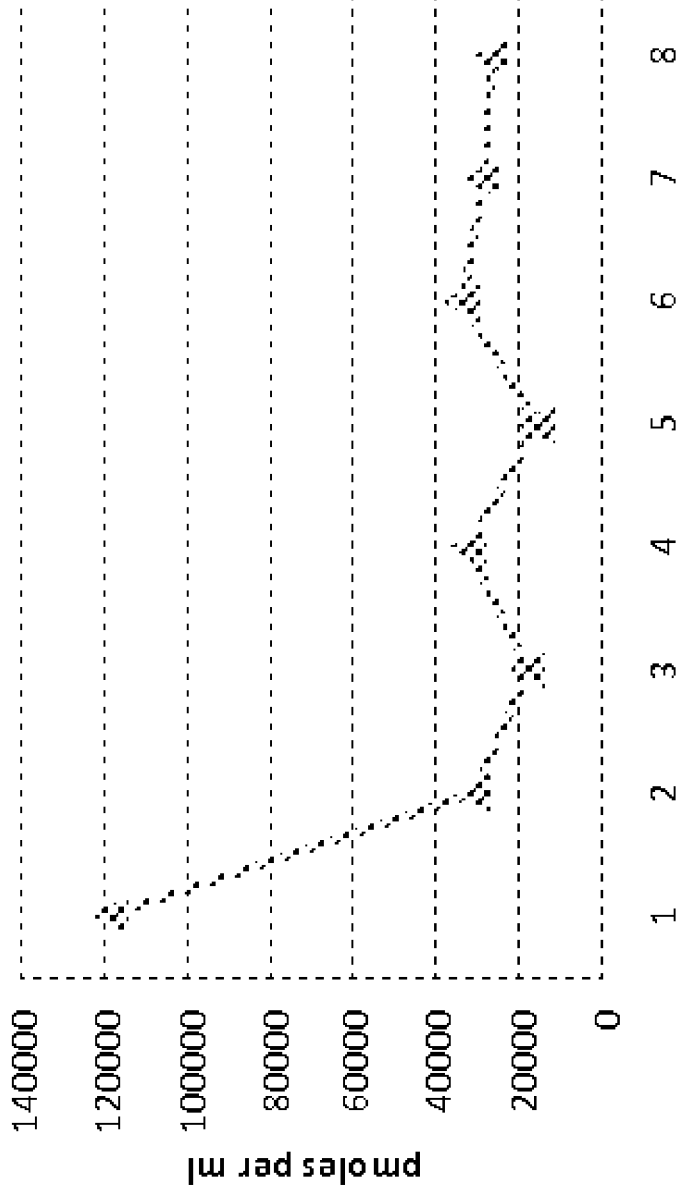
FIG. 20B illustrates monitoring of therapy in an individual by administration of an agent useful for treating MPS in urine samples.

FIG. 18A illustrates monitoring of therapy in an individual by administration of an agent useful for treating MPS in serum samples. FIG. 18B illustrates monitoring of therapy in an individual by administration of an agent useful for treating MPS in urine samples. FIG. 19A illustrates monitoring of therapy in an individual by administration of an agent useful for treating MPS in serum samples. FIG. 19B illustrates monitoring of therapy in an individual by administration of an agent useful for treating MPS in urine samples. FIG. 20A illustrates monitoring of therapy in an individual by administration of an agent useful for treating MPS in serum samples. FIG. 20B illustrates monitoring of therapy in an individual by administration of an agent useful for treating MPS in urine samples.

Disorders

Disorders associated with the abnormal degradation, biosynthesis and/or accumulation of glycosaminoglycans useful in the treatment and diagnostic methods and processes described herein include any disorder wherein accumulation of glycosaminoglycans and/or fragments thereof can be detected in a biological sample taken from an individual suffering from such a disorder. As discussed herein, disorders associated with abnormal glycosaminoglycan degradation, biosynthesis, and/or accumulation include e.g., lysosomal storage diseases. In specific embodiments, a lysosomal storage disease is mucopolysaccharidosis (MPS). In some embodiments, a mucopolysaccharidosis (MPS) is MPS I, MPS II, MPS IIIA, MPS IIIB, MPS IIIC, MPS IIID, MPS IVA, MPS IVB, MPS VI, MPS VII, MPS IX, or a combination thereof. In some embodiments, a MPS is Hunter's disease. In certain embodiments, Hunter's disease causes an accumulation of dermatan sulfate and heparan sulfate glycosaminoglycans. In certain instances, the accumulation of dermatan sulfate and heparan sulfate glycosaminoglycans in Hunter's disease is associated with a deficiency in a sulfatase. In some embodiments, the MPS is Hurler's disease. In certain instances, Hurler's disease causes an accumulation of dermatan sulfate and heparan sulfate glycosaminoglycans. In some instances, the accumulation of dermatan sulfate and heparan sulfate glycosaminoglycans in Hurler's disease is associated with a deficiency in an iduronidase.

In some embodiments, a disorder associated with abnormal glycosaminoglycan degradation, biosynthesis and/or accumulation is undesired angiogenesis (e.g., angiogenesis associated with cancer, diabetic blindness, age-related macular degeneration, rheumatoid arthritis, or psoriasis), insufficient angiogenesis (e.g., coronary artery disease, stroke, or delayed wound healing), amyloidosis, a spinal cord injury, hypertriglyceridemia, inflammation, or a wound.

In some instances, amyloidosis is present in various diseases including, e.g., Alzheimer's disease, Parkinson's disease, type-2 diabetes, Huntington's disease, spongiform encephalopathies (Creutzfeld-Jakob, Kuru, Mad Cow), diabetic amyloidosis, rheumatoid arthritis, juvenile chronic arthritis, Ankylosing spondylitis, psoriasis, psoriatic arthritis, adult still disease, Becet syndrome, famalial Mediterranean fever, Crohn's disease, leprosy, osteomyelitis, tuberculosis, chronic bronciectasis, Castleman disease, Hodgkin's disease, renal cell carcinoma, carcinoma of the gut, lung or urogenital tract. In some instances, the Alzheimer's disease is associated with changes in the content and structure of keratan sulfate.

In some embodiments, disorders associated with abnormal glycosaminoglycan accumulation include disorders associated with abnormal biosynthesis (e.g., polymerization and/or sulfation) of glycosaminoglycans. In certain instances, the abnormal biosynthesis of glycosaminoglycans results in glycosaminoglycans that are not readily degraded by normal glycosaminoglycan degrading enzymes. In some instances, disorders associated with abnormal GAG biosynthesis include osteoarthritis. In certain instances, osteoarthritis is associated with changes in sulfation of chondroitin sulfate, changes in length of chondroitin sulfate, changes in expression levels of chondroitin sulfate, or any combination thereof. In some instances, osteoarthritis is associated abnormal chondroitin sulfate sulfotransferase. In certain instances, the osteoarthritis is associated with changes in sulfation of dermatan sulfate, changes in length of dermatan sulfate, changes in expression levels of dermatan sulfate, or any combination of thereof. In certain instances, the osteoarthritis is associated with changes in sulfation of keratan sulfate, changes in length of keratan sulfate, changes in expression levels of keratan sulfate, or any combination of thereof.

In some embodiments, a disorder associated with abnormal glycosaminoglycan degradation, biosynthesis and/or accumulation is macular corneal dystrophy. In some instances, macular corneal dystrophy is associated with low amounts of keratan sulfate. In more specific embodiments, the keratan sulfate levels are due to failure to initiate keratan sulfate synthesis, polymerize the keratan sulfate chain length, or any combination thereof.

In some embodiments, a disorder associated with abnormal glycosaminoglycan degradation, biosynthesis and/or accumulation is an infectious or viral disease. In some embodiments, the infectious or viral disease includes herpes, diphtheria, papilloma virus, hepatitis, HW, coronavirus, or adenovirus.

In some embodiments, a disorder associated with abnormal glycosaminoglycan degradation, biosynthesis and/or accumulation is a cancer. In certain embodiments, the cancer is breast cancer, ovarian cancer, colorectal cancer, cervical cancer, pancreatic cancer, gastric cancer, esophageal cancer, head and neck cancer, hepatocellular cancer, prostate cancer, melanoma, osteosarcoma, endometrial cancer, multiple myeloma, gastric cancer, lung cancer, glioma, and non-Hodgkin lymphoma.

In certain instances, cancer is associated with abnormal heparan sulfate depolymerization and degradation that results in unbound, accumulated heparan sulfate. In some instances, abnormal heparan sulfate depolymerization and degradation is associated with melanomas, gliomas, multiple myelomas, ovarian, breast, colon, cervical, pancreatic, gastric, and esophageal cancers. In certain instances, abnormal heparan sulfate depolymerization and degradation contributes to angiogenesis, metastasis and growth factor mobilization. In some instances, the abnormal heparan sulfate depolymerization and degradation is from increased activity of a heparanase.

In certain instances, cancer is associated with abnormal heparan sulfate sulfation that results in accumulated heparan sulfate. In some instances, abnormal heparan sulfate sulfation is associated with colon carcinoma, myeloma, ovarian cancer, hepatocellular carcinoma, head and neck squamous cell carcinoma and prostate cancer. In some instances, heparan sulfate sulfation is decreased in certain cancers, while in other embodiments, the heparan sulfate sulfation is increased. In some instances, abnormal heparan sulfate sulfation is caused by abnormal heparan sulfate sulfotransferase function.

In certain instances, cancer is associated with abnormal chondroitin sulfate sulfation. In more specific embodiments, the abnormal chondroitin sulfate sulfation is associated with lung cancer. In some instances, the chondroitin sulfate sulfation is increased in certain cancers. In certain instances, the abnormal chondroitin sulfate sulfation is caused by abnormal chondroitin sulfate sulfotransferase function. In some instances, increased production of chondroitin sulfate is associated in breast cancer, melanoma, and transformed fibroblasts.

In certain instances, cancer is associated with dermatan sulfate epimerase expression. In some instances, the dermatan sulfate epimerase expression is increased in squamous cell carcinoma, glioma, gynecological cancer, pancreatic cancer, colorectal carcinoma, and prostate cancer. In certain instances, the cancer is associated with accumulation of dermatan sulfate levels. In some instances, the dermatan sulfate levels are increased in pancreatic cancer.

In certain instances, cancer is associated with abnormal keratan sulfate sulfation. In some instances, the abnormal keratan sulfate sulfation is associated with glioblastomas. In certain instances, abnormal keratan sulfate sulfation is caused by abnormal keratan sulfate sulfotransferase function. In some instances, keratan sulfate expression is increased in glioblastomas.

In certain instances, cancer is associated with abnormal hyaluronan accumulation. In some instances, abnormal hyaluronan accumulation is associated with breast cancer, prostate cancer, aggressive subtypes of non-Hodgkin lymphoma, and colorectal cancer. In certain instances, hyaluronan accumulation contributes to metastasis of certain cancers. In some instances, the hyaluronan accumulation results from the overexpression of a hyaluronan synthase.

Drug Screens

Provided in certain embodiments herein is a process for identifying an agent that inhibits the accumulation of glycosaminoglycans in a cell, the process comprising:
a. contacting a plurality of mammalian cells with a compound, the plurality of mammalian cells being of a cell line that accumulates an abnormal amount of glycosaminoglycans;
b. incubating the mammalian cells with the compound;
c. characterizing, within a sample from the plurality of mammalian cells, a population of glycosaminoglycans that have been tagged with a detectable label at the reducing end of each glycosaminoglycan; and
d. displaying or recording a characterization of the population of tagged glycosaminoglycans.

In certain embodiments, the cell is present in an individual (e.g., a human or other mammal) and is incubated at body temperature. In some embodiments, the cell line that accumulates an abnormal amount of glycosaminoglycans being a mucopolysaccharidosis (MPS) cell line (e.g., a human MPS cell line). In more specific embodiments, the MPS cell line is a cell line for MPS I, MPS II, MPS IIIA, MPS IIIB, MPS IIIC, MPS IIID, MPS IVA, MPS IVB, MPS VI, MPS VII, MPS IX, or a combination thereof. In some embodiments, the human MPS cell line is present in a human or other mammal. In some embodiments, inhibitors of the accumulation of glycosaminoglycans are compounds that reduce the rate of accumulation of glycosaminoglycans in the cell, and/or agents that reduce the total amount of glycosaminoglycans accumulated in the cell (i.e., diminish the amount of glycosaminoglycan that has been accumulated in the cell). Agents that are optionally tested for the screening process described herein include any compound such as, by way of non-limiting example, a polynucleotide (e.g., siRNA), a polypeptide, or a small molecule compound (e.g., having a molecular weight of less than 2,000 g/mol).

EXAMPLES

Example 1

Purification

The biological sample (cells, tissue, blood, serum, or the like) is homogenized and solubilized in 0.1-1.0 N NaOH or acetic acid and then neutralized with acetic acid or NaOH. Next a small sample is taken to measure protein content of the sample using standard methods. 0.01-0.5 mg/mL protease (trypsin, chymotrypsin, pepsin, pronase, papain, or elastase) is treated in 0.1-0.5 M NaCl, 0.01-0.1 M NaOAc, at pH 5.5-7.5 and 25-40 C for 1-24 hours. The sample is diluted to reduce the ionic strength and loaded onto an ion exchange column in 5-100 mM NaOAc pH 5-7 with 0-300 mM NaCl. After washing, the bound glycosaminoglycans are eluted with 5-100 mM NaOAc pH 5-7 with 0.8-3 M NaCl. The eluted glycans are then concentrated and desalted by ethanol precipitation, size exclusion, or other methods. The purified glycans are dried for further analysis.

Example 2

Tagging

Dried glycan sample is re-suspended in 2-100 µL 0.003-0.1 M AB, AA, AMAC, or Bodipy dye and incubated at room temperature for 1-120 minutes. Next, the reaction is initiated with 2-100 µL 1 M NaCNBH$_4$ and the reaction is allowed to proceed at 25-100 C Example 3

Detecting

The HPLC method used is run on HPLC using an ion exchange resin (such as a Nucleogen 60-7, ProTex DEAE, or Tsk Gel DEAE-NPR) column running at 0.1-2 mL/min. The sample is loaded on the column that was equilibrated in 5 to 100 mM sodium acetate pH 4-8 running at 0.1-2 mL/min. A gradient from 0-0.4 to 0.5-3 M NaCl is completed and the column is held in NaCl from 5-10 min.

FIG. 11 illustrates that the fluorescent dye elutes at 12 minutes in the methanol wash, while the fluorescently tagged glycans elute in the NaCl gradient (not visible at the scale in the figure).

Figure 12:
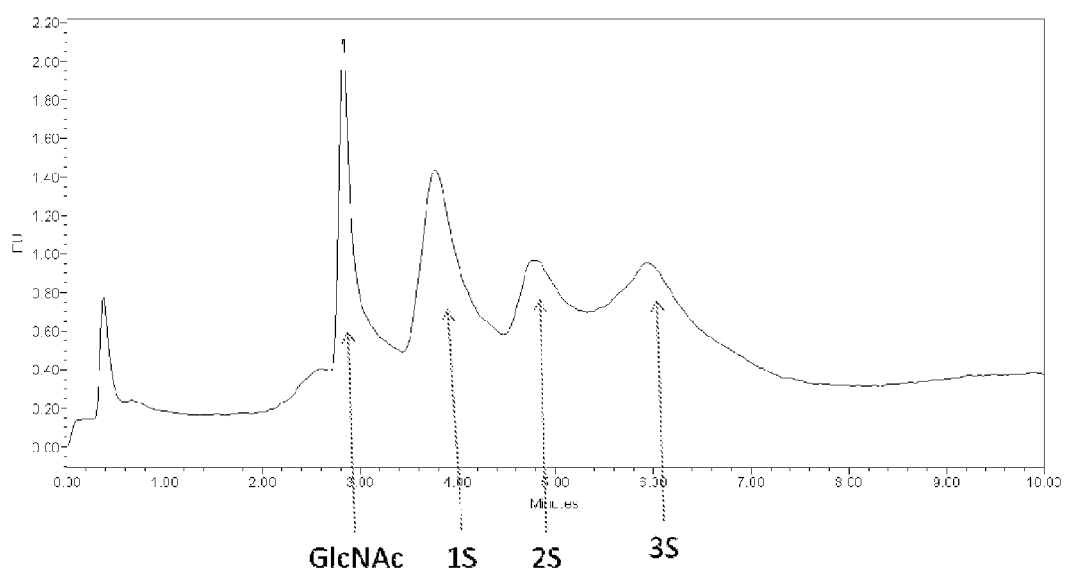
FIG. 12 illustrates the elution of tagged glycosaminoglycans.

Characterization of the HPLC system demonstrates that fluorescently tagged glycosaminoglycans eluted from the column in order of negative charge density. As illustrated in FIG. 12, non-sulfated glycans elute at 3 minutes, while glycans with 1, 2, or 3 sulfates per disaccharide elute at 4, 5, and 6 minutes, respectively.

Figure 13:
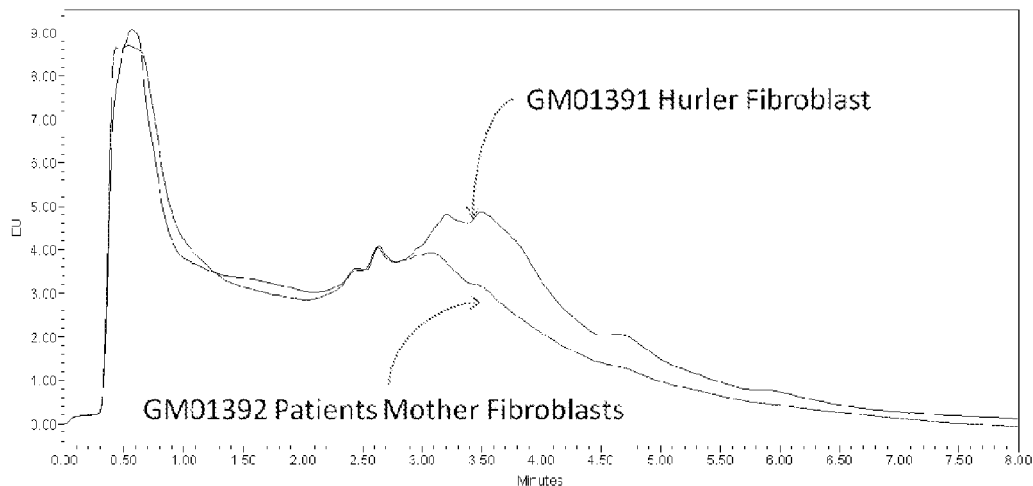
FIG. 13 illustrates the elution of tagged glycosaminoglycans in an MPS sample.

MPS I is caused by a mutation in the gene encoding the lysosomal iduronidase responsible for the degradation of glycosaminoglycans. Human MPS I fibroblasts (NIGMS Cell Repository, GM01391) and fibroblasts from the MPS I patients mother (GM01392) are cultured and accumulating glycans are prepared, labeled, and analyzed as described above. As shown in FIG. 13, the MPS I cell line (GM01391) shows an increase in flourescent tagged material (glycan ends) eluting around 3.5 minutes. This peak corresponds to the low level of glycosaminoglycan accumulation that occurs in short term cultures of MPS cells. The glycan accumulation is quantified by measuring the area under the curve or by other techniques.

Figure 14:
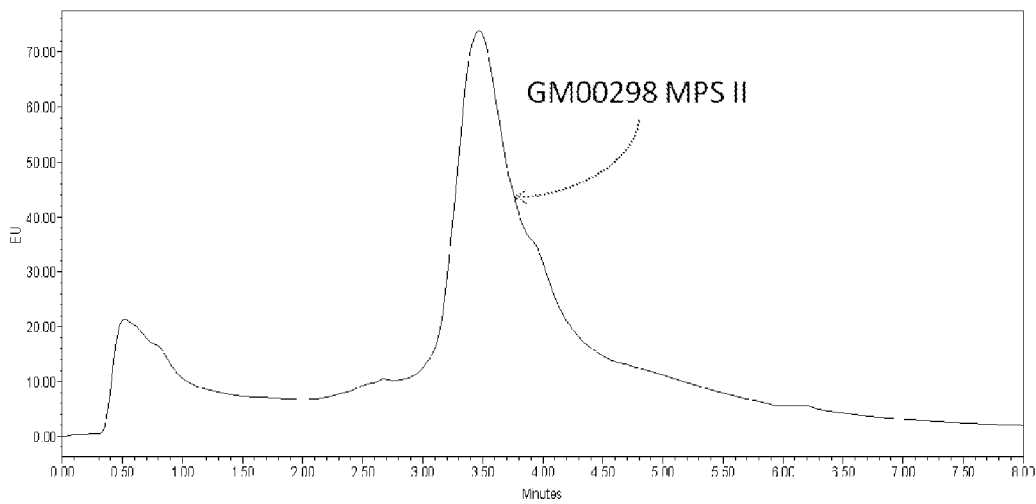
FIG. 14 illustrates the elution of tagged glycosaminoglycans in an MPS sample.

MPS II is caused by a mutation in the gene encoding the lysosomal 2-sulfatase responsible for the degradation of glycosaminoglycans. Human MPS II fibroblasts (NIGMS Cell Repository, GM00298) are cultured and accumulating glycans are prepared, labeled, and analyzed as described above. As shown in FIG. 14, an accumulation of fluorescent tagged glycan ends is detected and is optionally quantified.

MPS IIIB is caused by a mutation in the gene encoding the lysosomal N-acetylglucosaminidase responsible for the degradation of glycosaminoglycans. Liver tissue from MPS IIIB mice is processed, labeled, and analyzed as described above. As shown in FIG. 15, in this tissue type the glycosaminoglycan accumulation is very significant. Additionally, mild accumulation of less charged glycans eluting around 1 minute are also observed.

Example 4

GAGs purified from MPS cells are fluorescently tagged on their free reducing ends and analyzed by HPLC. The fluorescently labeled GAG fragments were quantified by HPLC on a DEAE column eluted with a NaCl gradient. This method resolves the GAGs based on their charge density, with heparan sulfate fragments eluting at 3.5 minutes. FIG. 16 illustrates the amount GAGs present in tissues from MPS mice, detected following tagging the reducing end of the GAGs with a fluorescent label.

Example 5

MPS I dogs were treated with intrathecal and IV rhIDU. IV treatment: all dogs received 0.58 mg/kg from baseline until animal sacrificed for post-mortem tissue analysis. Intrathecal treatment: high dose group—1.0 mg/kg (monthly for four months); low dose group—0.46 mg/kg (monthly for four months). Substantial differences were observed between baseline, treated, and wild type (normal) GAG levels in biological samples (e.g., in CSF and serum). Experiments demonstrated small sample size requirements, including the use of 50 µL or less. These methods successfully differentiated between baseline, treated, and wild type (normal) levels of GAG in biological samples (e.g., CSF).

Urine, CSF and serum samples were taken at baseline and at monthly intervals, including immediately prior to dose delivery and at end of the study. Detection methods utilized were as described in Examples 1-4. FIG. 17 illustrates serum GAG levels in MPS I dogs treated with IV/IT rhIDU.

Example 6

MPS dogs all received 0.58 mg/kg IV Aldurazyme weekly through the study. Specific parameters for the therapy were as set forth in Dickson, P. et al. The Journal of Clinical Investigation (August 2008) 118(8):2868-76, which is incorporated herein by reference in its entirety. The first sample for each dog was taken before treatment was initiated. Subsequent samples were generally taken monthly. The variability in the response to therapy reflects the different severities and responses in each dog. For example, different effects of therapy can be observed in similar biological sample types in FIGS. 18A, 19A, and 20A (serum), or FIGS. 18B, 19B, and 20B (urine).

What is claimed is:

1. A process for diagnosing or determining the severity of abnormal glycosaminoglycan accumulation or a disorder associated with abnormal glycosaminoglycan degradation in an individual, the process comprising the steps of:
   (a) quantifying with an analytical device, within or from within a test biological sample from the individual, the amount of a population of glycosaminoglycans that have been tagged with a detectable label at the reducing end of the glycosaminoglycan; and
   (b) displaying or recording a quantification of the amount of the population of tagged glycosaminoglycans
whereby the quantification of the population of tagged glycosaminoglycans is utilized to determine the presence, identity and/or severity of the disease or condition.

2. The process of claim 1, further comprising the step of:
   (a) collecting from the individual a biological sample that comprises glycosaminoglycans; and
   (b) tagging the reducing end of a representative portion of the glycosaminoglycans in the population of glycosaminoglycans within the biological sample with the detectable label to provide the population of tagged glycosaminoglycans.

3. The process of claim 1, wherein the one or more different types of tagged glycosaminoglycans are one or more different tagged heparan sulfate fragments.

4. The process of claim 1, wherein quantifying the amount of a population of glycosaminoglycans that have been tagged comprises separately quantifying the amount of a population of one or more different tagged chondroitin sulfate fragments, one or more different tagged dermatan sulfate fragments, one or more different tagged heparan sulfate fragments, one or more different tagged keratan sulfate fragments, one or more different tagged hyaluronan fragments, or a combination thereof.

5. The process of claim 1, further comprising purifying the glycosaminoglycans from the test biological sample prior to tagging the reducing end of the glycosaminoglycans.

6. The process of claim 1, wherein the detectable label is a mass label, affinity label, radiolabel, chromophore, or a fluorescent label.

7. The process of claim 1, wherein the disorder is a disorder associated with abnormal glycosaminoglycan degradation and is a lysosomal storage disease.

8. The process of claim 7, wherein the disorder associated with abnormal glycosaminoglycan degradation is mucopolysaccharidosis (MPS).

9. The process of claim 8, wherein the mucopolysaccharidosis (MPS) is MPS I, MPS II, MPS IIIA, MPS IIIB, MPS IIIC, MPS IIID, MPS IVA, MPS IVB, MPS VI, MPS VII, MPS IX, or a combination thereof.

10. The process of claim 1, wherein the quantification of the population of tagged glycosaminoglycans is utilized to monitor the treatment of disorders associated with the abnormal degradation, biosynthesis and / or accumulation of glycosaminoglycans (GAGs), or a disorder associated therewith.

11. The process of claim 1, wherein the disorder associated with abnormal glycosaminoglycan accumulation is cancer.

* * * * *